(12) United States Patent
Thapliyal et al.

(10) Patent No.: US 9,737,323 B2
(45) Date of Patent: *Aug. 22, 2017

(54) SYSTEMS AND METHODS FOR IMAGING AND ABLATING BODY TISSUE

(71) Applicant: VytronUS, Inc., Sunnyvale, CA (US)

(72) Inventors: Hira V. Thapliyal, Los Altos, CA (US); David A. Gallup, Alameda, CA (US); James W. Arenson, Woodside, CA (US); John Paul Mohr, III, Aptos, CA (US); Tim Proulx, Santa Cruz, CA (US); Robert A. Brommer, Fremont, CA (US)

(73) Assignee: VytronUS, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/907,412

(22) Filed: May 31, 2013

(65) Prior Publication Data
US 2013/0261455 A1    Oct. 3, 2013

Related U.S. Application Data

(63) Continuation of application No. 12/620,287, filed on Nov. 17, 2009, now Pat. No. 8,475,379.
(Continued)

(51) Int. Cl.
*A61B 8/00* (2006.01)
*A61B 17/32* (2006.01)
(Continued)

(52) U.S. Cl.
CPC .... *A61B 17/320068* (2013.01); *A61B 8/0883* (2013.01); *A61B 8/12* (2013.01);
(Continued)

(58) Field of Classification Search
CPC .. A61B 2018/00023; A61B 2019/5278; A61B 2090/3782; A61B 8/12;
(Continued)

(56) References Cited

U.S. PATENT DOCUMENTS

| 4,641,649 A | 2/1987 | Walinsky et al. |
| 4,757,820 A | 7/1988 | Itoh |

(Continued)

FOREIGN PATENT DOCUMENTS

| DE | 10037660 A | 2/2002 |
| WO | WO 99/02096 A1 | 1/1999 |

(Continued)

OTHER PUBLICATIONS

A new treatment for atrial fibrillation? Feb. 2006, Medical Device & Diagnostic Industry, Medical Device Link, http://www.devicelink.com/mddi/archive/06/02/013.html.
(Continued)

*Primary Examiner* — Ruth S Smith
(74) *Attorney, Agent, or Firm* — The Mueller Law Office, P.C.

(57) ABSTRACT

A transducer subassembly with combined imaging and therapeutic capabilities is disclosed. The subassembly includes heat sinks that are configured to maintain the transducer at a low operating temperature so that the transducer operates at high efficiency and also can handle a wider range of frequencies. The subassembly is also configured to allow cooling fluid to flow past the transducer element. One heat sink in the subassembly also acts as an acoustic matching layer and another heat sink acts as a backing Alternatively, the second heat sink which acts as a backing is optional. The transducer is configured to transmit at one power level for imaging, and at a second power level for ablating. The transducer may comprise sub-elements transmitting at different power levels. The subassembly may be operated at one power level for imaging and a second power level for ablating.

24 Claims, 10 Drawing Sheets

Related U.S. Application Data

(60) Provisional application No. 61/115,403, filed on Nov. 17, 2008.

(51) Int. Cl.
*A61N 7/02* (2006.01)
*A61B 8/08* (2006.01)
*A61B 8/12* (2006.01)
*A61B 18/00* (2006.01)
*A61B 90/00* (2016.01)

(52) U.S. Cl.
CPC ............ *A61B 8/445* (2013.01); *A61B 8/4494* (2013.01); *A61N 7/022* (2013.01); *A61B 2018/00023* (2013.01); *A61B 2090/3782* (2016.02)

(58) Field of Classification Search
CPC .................. A61B 8/445; A61B 8/4488; A61B 17/320068; A61B 8/0883; A61B 8/4494; A61N 7/022
See application file for complete search history.

(56) References Cited

U.S. PATENT DOCUMENTS

| | | | |
|---|---|---|---|
| 5,164,920 A * | 11/1992 | Bast et al. | 367/140 |
| 5,246,438 A | 9/1993 | Langberg | |
| 5,295,484 A | 3/1994 | Marcus et al. | |
| 5,314,466 A | 5/1994 | Stern et al. | |
| 5,405,346 A | 4/1995 | Grundy et al. | |
| 5,471,988 A | 12/1995 | Fujio et al. | |
| 5,560,362 A * | 10/1996 | Sliwa et al. | 600/439 |
| 5,718,241 A | 2/1998 | Ben-Haim et al. | |
| 5,735,811 A | 4/1998 | Brisken | |
| 5,879,314 A | 3/1999 | Peterson et al. | |
| 5,908,418 A * | 6/1999 | Dority et al. | 606/40 |
| 6,012,457 A | 1/2000 | Lesh | |
| 6,024,740 A | 2/2000 | Lesh et al. | |
| 6,050,943 A | 4/2000 | Slayton et al. | |
| 6,052,576 A | 4/2000 | Lambourg | |
| 6,064,902 A | 5/2000 | Haissaguerre et al. | |
| 6,117,101 A | 9/2000 | Diederich et al. | |
| 6,161,543 A | 12/2000 | Cox et al. | |
| 6,164,283 A | 12/2000 | Lesh | |
| 6,237,605 B1 | 5/2001 | Vaska et al. | |
| 6,245,064 B1 | 6/2001 | Lesh et al. | |
| 6,245,095 B1 | 6/2001 | Dobak, III et al. | |
| 6,251,129 B1 | 6/2001 | Dobak, III et al. | |
| 6,251,130 B1 | 6/2001 | Dobak, III et al. | |
| 6,254,599 B1 | 7/2001 | Lesh et al. | |
| 6,261,312 B1 | 7/2001 | Dobak, III et al. | |
| 6,277,116 B1 | 8/2001 | Utely et al. | |
| 6,305,378 B1 | 10/2001 | Lesh | |
| 6,311,090 B1 | 10/2001 | Knowlton | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,379,378 B1 | 4/2002 | Werneth et al. | |
| 6,383,151 B1 | 5/2002 | Diederich et al. | |
| 6,387,089 B1 | 5/2002 | Kreindel et al. | |
| 6,416,511 B1 | 7/2002 | Lesh et al. | |
| 6,468,296 B1 | 10/2002 | Dobak, III et al. | |
| 6,474,340 B1 | 11/2002 | Vaska et al. | |
| 6,475,231 B2 | 11/2002 | Dobak, III et al. | |
| 6,478,811 B1 | 11/2002 | Dobak, III et al. | |
| 6,478,812 B2 | 11/2002 | Dobak, III et al. | |
| 6,484,727 B1 | 11/2002 | Vaska et al. | |
| 6,491,039 B1 | 12/2002 | Dobak, III et al. | |
| 6,491,716 B2 | 12/2002 | Dobak, III et al. | |
| 6,500,121 B1 | 12/2002 | Slayton et al. | |
| 6,500,174 B1 | 12/2002 | Maguire et al. | |
| 6,502,576 B1 | 1/2003 | Lesh | |
| 6,514,244 B2 | 2/2003 | Pope et al. | |
| 6,514,249 B1 | 2/2003 | Maguire et al. | |
| 6,517,536 B2 | 2/2003 | Hooven et al. | |
| 6,529,756 B1 | 3/2003 | Phan et al. | |
| 6,533,804 B2 | 3/2003 | Dobak, III et al. | |
| 6,540,771 B2 | 4/2003 | Dobak, III et al. | |
| 6,542,781 B1 | 4/2003 | Koblish et al. | |
| 6,546,935 B2 | 4/2003 | Hooven | |
| 6,547,788 B1 | 4/2003 | Maguire et al. | |
| 6,551,349 B2 | 4/2003 | Lasheras et al. | |
| 6,576,001 B2 | 6/2003 | Werneth et al. | |
| 6,585,752 B2 | 7/2003 | Dobak, III et al. | |
| 6,592,576 B2 | 7/2003 | Andrews et al. | |
| 6,595,989 B1 | 7/2003 | Schaer | |
| 6,599,288 B2 | 7/2003 | Maguire et al. | |
| 6,602,276 B2 | 8/2003 | Dobak, III et al. | |
| 6,605,084 B2 | 8/2003 | Acker et al. | |
| 6,607,502 B1 | 8/2003 | Maguire et al. | |
| 6,607,527 B1 | 8/2003 | Ruiz et al. | |
| 6,613,046 B1 | 9/2003 | Jenkins et al. | |
| 6,635,054 B2 | 10/2003 | Fjield et al. | |
| 6,645,199 B1 | 11/2003 | Jenkins et al. | |
| 6,645,202 B1 | 11/2003 | Pless et al. | |
| 6,648,908 B2 | 11/2003 | Dobak, III et al. | |
| 6,652,515 B1 | 11/2003 | Maguire et al. | |
| 6,652,517 B1 | 11/2003 | Hall et al. | |
| 6,666,614 B2 | 12/2003 | Fechter et al. | |
| 6,666,858 B2 | 12/2003 | Lafontaine | |
| 6,669,655 B1 | 12/2003 | Acker et al. | |
| 6,669,687 B1 | 12/2003 | Saadat | |
| 6,676,688 B2 | 1/2004 | Dobak, III et al. | |
| 6,676,689 B2 | 1/2004 | Dobak, III et al. | |
| 6,676,690 B2 | 1/2004 | Werneth | |
| 6,685,732 B2 | 2/2004 | Kramer | |
| 6,689,128 B2 | 2/2004 | Sliwa, Jr. et al. | |
| 6,692,488 B2 | 2/2004 | Dobak, III et al. | |
| 6,695,873 B2 | 2/2004 | Dobak, III et al. | |
| 6,701,931 B2 | 3/2004 | Sliwa, Jr. et al. | |
| 6,702,842 B2 | 3/2004 | Dobak, III et al. | |
| 6,711,444 B2 | 3/2004 | Koblish | |
| 6,719,755 B2 | 4/2004 | Sliwa, Jr. et al. | |
| 6,745,080 B2 | 6/2004 | Koblish | |
| 6,752,805 B2 | 6/2004 | Maguire et al. | |
| 6,758,847 B2 | 7/2004 | Maguire | |
| 6,763,722 B2 | 7/2004 | Fjield et al. | |
| 6,780,183 B2 | 8/2004 | Jimenez, Jr. et al. | |
| 6,786,218 B2 | 9/2004 | Dobak, III | |
| 6,805,128 B1 | 10/2004 | Pless et al. | |
| 6,805,129 B1 | 10/2004 | Pless et al. | |
| 6,814,733 B2 | 11/2004 | Schwartz et al. | |
| 6,840,936 B2 | 1/2005 | Sliwa, Jr. et al. | |
| 6,858,026 B2 | 2/2005 | Sliwa, Jr. et al. | |
| 6,869,431 B2 | 3/2005 | Maguire et al. | |
| 6,872,205 B2 | 3/2005 | Lesh et al. | |
| 6,889,694 B2 | 5/2005 | Hooven | |
| 6,893,438 B2 | 5/2005 | Hall et al. | |
| 6,896,673 B2 | 5/2005 | Hooven | |
| 6,899,710 B2 | 5/2005 | Hooven | |
| 6,899,711 B2 | 5/2005 | Stewart et al. | |
| 6,904,303 B2 | 6/2005 | Phan et al. | |
| 6,905,494 B2 | 6/2005 | Yon et al. | |
| 6,905,498 B2 | 6/2005 | Hooven | |
| 6,905,509 B2 | 6/2005 | Dobak, III et al. | |
| 6,908,464 B2 | 6/2005 | Jenkins et al. | |
| 6,920,883 B2 | 7/2005 | Bessette et al. | |
| 6,923,806 B2 | 8/2005 | Hooven et al. | |
| 6,923,808 B2 | 8/2005 | Taimisto | |
| 6,929,639 B2 | 8/2005 | Lafontaine | |
| 6,932,811 B2 | 8/2005 | Hooven et al. | |
| 6,949,095 B2 | 9/2005 | Vaska et al. | |
| 6,949,097 B2 | 9/2005 | Stewart et al. | |
| 6,953,460 B2 | 10/2005 | Maguire et al. | |
| 6,954,977 B2 | 10/2005 | Maguire et al. | |
| 6,955,173 B2 | 10/2005 | Lesh | |
| 6,964,660 B2 | 11/2005 | Maguire et al. | |
| 6,966,908 B2 | 11/2005 | Maguire et al. | |
| 6,971,394 B2 | 12/2005 | Sliwa, Jr. et al. | |
| 6,974,454 B2 | 12/2005 | Hooven | |
| 6,984,233 B2 | 1/2006 | Hooven | |
| 6,997,925 B2 | 2/2006 | Maguire et al. | |
| 7,001,378 B2 | 2/2006 | Yon et al. | |

(56) References Cited

U.S. PATENT DOCUMENTS

| | | |
|---|---|---|
| 7,001,415 B2 | 2/2006 | Hooven |
| 7,044,135 B2 | 5/2006 | Lesh |
| 7,063,682 B1 | 6/2006 | Whayne et al. |
| 7,142,905 B2 | 11/2006 | Slayton et al. |
| 7,275,450 B2 | 10/2007 | Hirai et al. |
| 7,285,116 B2 | 10/2007 | de la Rama et al. |
| 7,306,593 B2 | 12/2007 | Keidar et al. |
| 7,393,325 B2 | 7/2008 | Barthe et al. |
| 2002/0087151 A1 | 7/2002 | Mody et al. |
| 2003/0050630 A1 | 3/2003 | Mody et al. |
| 2003/0050631 A1 | 3/2003 | Mody et al. |
| 2003/0229331 A1* | 12/2003 | Brisken et al. ............. 604/500 |
| 2005/0049582 A1 | 3/2005 | DeBenedictis et al. |
| 2005/0165388 A1 | 7/2005 | Bhola |
| 2005/0267453 A1 | 12/2005 | Wong et al. |
| 2006/0058707 A1 | 3/2006 | Barthe et al. |
| 2006/0122508 A1 | 6/2006 | Slayton et al. |
| 2007/0027445 A1 | 2/2007 | Gifford et al. |
| 2007/0265609 A1 | 11/2007 | Thapliyal et al. |
| 2007/0265610 A1* | 11/2007 | Thapliyal et al. ............. 606/27 |
| 2008/0039746 A1 | 2/2008 | Hissong et al. |
| 2008/0077200 A1 | 3/2008 | Bendett et al. |
| 2008/0194967 A1 | 8/2008 | Sliwa et al. |
| 2008/0262358 A1 | 10/2008 | Kaminski et al. |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0125198 A1 | 5/2010 | Thapliyal et al. |
| 2010/0152582 A1 | 6/2010 | Thapliyal et al. |

FOREIGN PATENT DOCUMENTS

| | | |
|---|---|---|
| WO | WO 2005/117734 A2 | 12/2005 |
| WO | WO 2005/117734 A3 | 2/2006 |
| WO | WO 2006/034000 A1 | 3/2006 |
| WO | WO 2006034000 A1 * | 3/2006 |

OTHER PUBLICATIONS

Bushberg, et al.; The essential physics of medical imaging. 2nd Ed.; Lippincott Williams & Wilkins; 2002; 491.

Cox, et al. Current status of the Maze procedure for the treatment of atrial fibrillation. Seminars in Thoracic & Cardiovascular Surgery. 2000; 12:15-19.

Cox, et al. Electrophysiologic basis, surgical development, and clinical results of the maze procedure for atrial flutter and atrial fibrillation. Advances in Cardiac Surgery. 1995; 6:1-67.

Cox, et al. Modification of the maze procedure for atrial flutter and atrial fibrillation. II, Surgical technique of the maze III procedure. Journal of Thoracic & Cardiovascular Surgery. 1995;110:485-95.

Cox, et al. The development of the Maze procedure for the treatment of atrial fibrillation. Seminars in Thoracic & Cardiovascular Surgery. 2000; 12:2-14.

European search report dated Oct. 19, 2012 for EP Application No. 09826990.5.

Gentry, et al. Integrated Catheter for 3-D Intracardiac Echocardiography and Ultrasound Ablation. IEEE Transactions on Ultrasonics, Ferroelectrics, and Frequency Control. 2004;51(7):800-808.

Gill. How to perform pulmonary vein isolation. Europace. 2004; 6(2):83-91.

Gillinov, et al. Atrial fibrillation: current surgical options and their assessment. Annals of Thoracic Surgery. 2002;74:2210-7.

Haissaguerre, et al. Spontaneous Initiation of Atrial Fibrillation by Ectopic Beats Originating in the Pulmonary Veins. New England J Med. 1998; 339:659-666.

International search report and written opinion dated Jan. 20, 2010 for PCT/US2009/064850.

Levinson. Endocardial Microwave Ablation: A New Surgical Approach for Atrial Fibrillation. The Heart urgery Forum. 2006.

Maessen, et al. Beating heart surgical treatment of atrial fibrillation with microwave ablation. Ann Thorac Surg. 2002; 74: 1160-8.

Nathan, et al. The junction between the left atrium and the pulmonary veins, an anatomic study of human hearts. Circulation. 1966; 34:412-422.

Office action dated May 9, 2012 for U.S. Appl. No. 12/620,287.

Office action dated Nov. 3, 2011 for U.S. Appl. No. 12/620,287.

Sueda, et al. Efficacy of a simple left atrial procedure for chronic atrial fibrillation in mitral valve operations. Ann Thorac Surg. 1997; 63:1070-1075.

Sueda, et al. Simple left atrial procedure for chronic atrial fibrillation associated with mitral valve disease. Ann Thorac Surg 1996; 62:1796-1800.

Ter Haar. Acoustic surgery. Physics Today. Dec. 2001; 54(12):29-34.

Notice of allowance dated Mar. 1, 2013 for U.S. Appl. No. 12/620,287.

\* cited by examiner

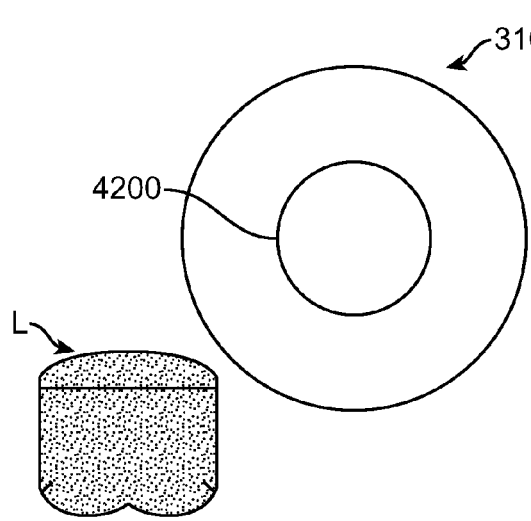
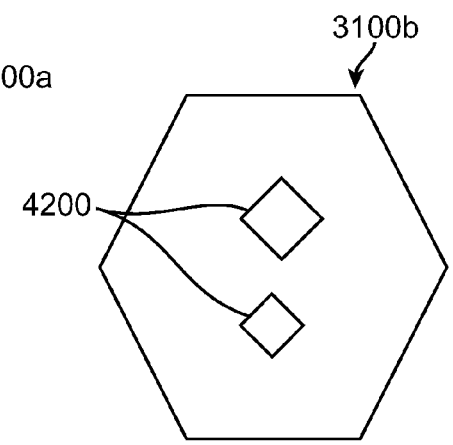
FIG. 2A  FIG. 2B
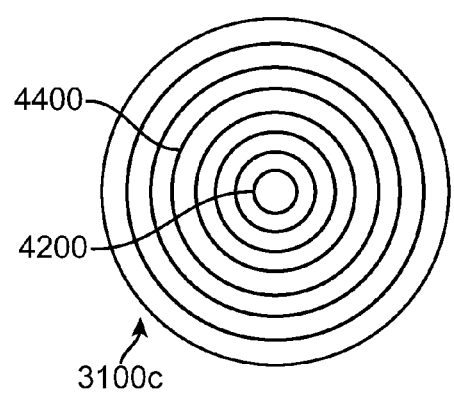
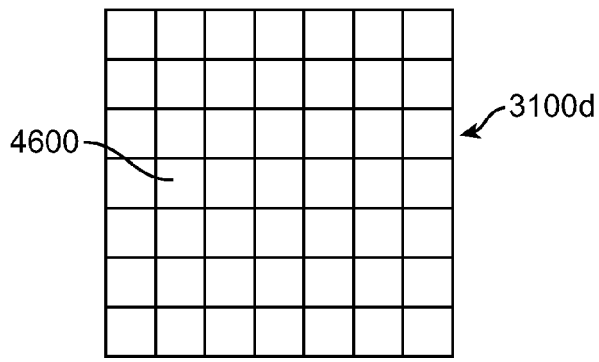
FIG. 2C  FIG. 2D

SYSTEMS AND METHODS FOR IMAGING AND ABLATING BODY TISSUE

CROSS-REFERENCE

The present application is a continuation of U.S. application Ser. No. 12/620,287 filed on Nov. 17, 2009, now U.S. Pat. No. 8,475,379, which is a non-provisional of, and claims the benefit of priority of U.S. Provisional Patent Application No. 61/115,403 filed Nov. 17, 2008, the entire contents of which are incorporated herein by reference.

The present application is related to U.S. Pat. No. 7,950,397 and U.S. Pat. No. 7,942,871 and copending U.S. patent application Ser. No. 12/480,929; Ser. No. 12/480,256; Ser. No. 12/483,174; Ser. No. 12/482,640; Ser. No. 12/505,326; Ser. No. 12/505,335; Ser. No. 12/609,759; Ser. No. 12/609,274; and Ser. No. 12/609,705. The present application is also related to U.S. Provisional Patent Application Nos. 61/148,809; and 61/254,997. The entire contents of each of the above referenced applications is incorporated herein by reference.

BACKGROUND OF THE INVENTION

1. Field of the Invention

The present application generally relates to systems and methods for creating ablation zones in human tissue. More specifically, the present application relates to transducer configurations used to create tissue lesions, and even more specifically to ultrasound transducers used to treat fibrillation of the heart. While the present application emphasizes treatment of atrial fibrillation, one of skill in the art will appreciate that this is not intended to be limiting, and that the systems and methods disclosed herein may also be used to treat other arrhythmias as well as to treating other conditions by creating lesions in tissue.

The condition of atrial fibrillation (AF) is characterized by the abnormal (usually very rapid) beating of the left atrium of the heart which is out of synch with the normal synchronous movement ('normal sinus rhythm') of the heart muscle. In normal sinus rhythm, the electrical impulses originate in the sino-atrial node ('SA node') which resides in the right atrium. The abnormal beating of the atrial heart muscle is known as 'fibrillation' and is caused by electrical impulses originating instead at points other than the SA node, for example, in the pulmonary veins (PV).

There are pharmacological treatments for this condition with varying degree of success. In addition, there are surgical interventions aimed at removing the aberrant electrical pathways from PV to the left atrium ('LA') such as the 'Cox-Maze III Procedure'. This procedure has been shown to be 99% effective but requires special surgical skills and is time consuming. Thus, there has been considerable effort to copy the Cox-Maze procedure using a less invasive percutaneous catheter-based approach. Less invasive treatments have been developed which involve use of some form of energy to ablate (or kill) the tissue surrounding the aberrant focal point where the abnormal signals originate in PV. The most common methodology is the use of radio-frequency ('RF') electrical energy to heat the muscle tissue and thereby ablate it. The aberrant electrical impulses are then prevented from traveling from PV to the atrium (achieving the 'conduction block') and thus avoiding the fibrillation of the atrial muscle. Other energy sources, such as microwave, laser, and ultrasound have been utilized to achieve the conduction block. In addition, techniques such as cryoablation, administration of ethanol, and the like have also been used. Some of these methods and devices are described below.

There has been considerable effort in developing catheter based systems for the treatment of AF using radiofrequency (RF) energy. One such method includes a catheter having distal and proximal electrodes at the catheter tip. The catheter can be bent in a coil shape, and positioned inside a pulmonary vein. The tissue of the inner wall of the PV is ablated in an attempt to kill the source of the aberrant heart activity.

Another source used in ablation is microwave energy. One such intraoperative device consists of a probe with a malleable antenna which has the ability to ablate the atrial tissue.

Still another catheter based method utilizes the cryogenic technique where the tissue of the atrium is frozen below a temperature of −60 degrees C. This results in killing of the tissue in the vicinity of the PV thereby eliminating the pathway for the aberrant signals causing the AF. Cryo-based techniques have also been a part of the partial Maze procedures described above. More recently, Dr. Cox and his group have used cryoprobes (cryo-Maze) to duplicate the essentials of the Cox-Maze III procedure.

More recent approaches for the treatment of AF involve the use of ultrasound energy. The target tissue of the region surrounding the pulmonary vein is heated with ultrasound energy emitted by one or more ultrasound transducers. One such approach includes a catheter distal tip portion equipped with a balloon and containing an ultrasound element. The balloon serves as an anchoring means to secure the tip of the catheter in the pulmonary vein. The balloon portion of the catheter is positioned in the selected pulmonary vein and the balloon is inflated with a fluid which is transparent to ultrasound energy. The transducer emits the ultrasound energy which travels to the target tissue in or near the pulmonary vein and ablates it. The intended therapy is to destroy the electrical conduction path around a pulmonary vein and thereby restore the normal sinus rhythm. The therapy involves the creation of a multiplicity of lesions around individual pulmonary veins as required.

Yet another catheter device using ultrasound energy includes a catheter having a tip with an array of ultrasound elements in a grid pattern for the purpose of creating a three dimensional image of the target tissue. An ablating ultrasound transducer is provided which is in the shape of a ring which encircles the imaging grid. The ablating transducer emits a ring of ultrasound energy at 10 MHz frequency.

While such ablation therapies alone are promising, it is preferred that devices and systems combine these ablation therapies with imaging capabilities in a single unit. It would be particularly useful to provide sensing or imaging (often used interchangeably) of the treatment region to properly position the ablation device relative to the treatment region, as well as to evaluate progression of the treatment. Such imaging assists the system or the operator to ensure that only the targeted tissue region is ablated. Furthermore, in a moving target such as heart tissue, the original target identified by imaging, can move and thus non-target tissue may be inadvertently ablated. Hence, contemporaneous (or almost contemporaneous) imaging and ablation minimizes the risk of ablating non-target tissue. Thus, one unmet need using ultrasound techniques for tissue ablation is to provide a device capable of both imaging as well as ablation.

Attaining this goal involves redesigning the key components of a conventional ultrasound ablation system to also provide an imaging function. Typically, ultrasound ablation is accomplished using a transducer assembly. The transducer assembly comprises a transducer element, commonly one or more piezoelectrically active elements such as lead zirconate titanate (PZT) crystals. The PZT crystals often include an acoustical (impedance) matching layer on the ablating face to facilitate efficient power transmission and to improve the imaging performance. Further, the crystals may be bonded to a backing on the non-ablative face to reflect or absorb any ultrasound beams in the appropriate direction. The conventional acoustic transducers which are typically employed for the therapeutic purposes are acoustically large, often single-crystal devices having a narrower bandwidth in the frequency domain than is required for good imaging performance. Although they are designed to efficiently transmit acoustic energy to the target tissue, crystal devices with narrow bandwidth have previously been viewed as unsuited for imaging. This has been due to the perceived inability of conventional ablation transducers to handle the bandwidth of the ultrasound frequencies that would be optimized for both imaging and ablation. While ablation can be achieved using a narrower range of frequencies, imaging is usually performed using a wide range of frequencies. Thus, it is desirable that the PZT be able to accommodate a wider bandwidth than used for ablation in order to accommodate the imaging bandwidth.

Wider transducer bandwidths are often achieved through the use of matching layers. Matching layers typically use materials with acoustic impedance between the acoustic impedances of the PZT and the tissue, and with a thickness approaching ¼ wavelength of the ultrasound frequency utilized. While matching layers are often used to improve the transmission of ultrasound from the PZT into the tissue, they also can be used to dampen the mechanical response of the PZT and broaden its bandwidth. This dampening can result in some reduction of transducer efficiency. Furthermore wide bandwidth transducers may be unable operate at high power levels because they cannot be cooled effectively, partly due to the thermally insulating properties of the matching layer. A conventional PZT transducer with a higher bandwidth may often be only 30%-50% efficient in converting the electrical energy to acoustic energy, and much of the energy is converted to heat and lost in the transducer assembly. In addition to the lack of efficiency in converting to ultrasound energy, the heat further reduces the PZT efficiency and may cause the PZT crystal to depole and stop functioning as a transducer.

Thus, an additional challenge is to cool the transducer to maintain a lower operating temperature than is presently provided for in commercially available systems. A cooled transducer can be driven harder, i.e., it can tolerate higher electric powers and produce higher acoustic powers. This higher acoustic output is useful in increasing the lesion size and/or reducing the amount of time required to create a lesion. Both of these attributes are important in the clinical application of treating AF.

One method of cooling the transducer is to take advantage of the power density and heat dissipation that are dependent on the size of the transducer. As the diameter (and corresponding surface area) of the transducer increases, the power density drops, and the heat dissipation per unit surface area also drops. If large enough, conventional cooling methods may suffice to keep the transducer cool. However, in a catheter suitable for ablation using an interventional approach, the transducer must necessarily be small and yet also be able to generate the power density levels required to ablate tissue. In such a transducer, size is not a suitable method of regulating the transducer's temperature. Thus, due to the small transducer size and consequent high power densities and low heat dissipation, alternative approaches are warranted for cooling the transducer.

One potential solution is the use of fluids to cool the transducer. Commonly, bodily fluids, such as blood flowing around the transducer, are used as a cooling fluid. However, blood tends to denature and collect around the transducer when heated. In addition to the attendant problems of possibly creating a clot in the atrium, the denatured blood may also adhere to the face of the transducer and create a layer of insulation, thereby further decreasing the performance of the transducer. In contrast, introduced (non-bodily) fluids such as saline or water do not have the same attendant problems as blood and are useful in maintaining lower transducer operating temperatures. However, in order to be effective, these introduced fluids have to be effectively transported to the entire transducer to cool all the faces of the transducer. If fluid transport is inadequate, the uncooled regions may develop "hot spots" that can impede the efficiency of the transducer.

While some devices, such as single crystal ultrasound therapy systems have been reported for both imaging and therapeutic purposes, none disclose a method for cooling the entire transducer. Other multi-crystal transducer assemblies are also available that circumvent the concerns of the single-crystal model. Some of these systems provide a method for cooling the back of the transducer crystals. However, none of these systems or methods include cooling of the entire transducer crystal. As mentioned above, it is important to cool all the faces of the transducer (front and the back). Cooling only part of the transducer may lead to "hot spots" on some areas of the transducer, thereby decreasing the efficiency of the transducer in a situation where both ablation and imaging are necessary.

To realize combined imaging and ablation capabilities, some systems have separate imaging and ablation units. For example one commercially available system includes a treatment and imaging system. This system comprises a probe with an ultrasound transducer adapted to obtain imaging information from a patient treatment region, and also a separate arm member to deliver ultrasonic energy to the treatment region. Naturally, these are bulky and not well suited for use in catheter based systems. A variant of the combined imaging and ablation units is using separate transducer elements for imaging and ablation. This approach suffers from many shortcomings including functionally, the ablated tissue is not identical to the imaged tissue, and structurally this configuration of discrete imaging and ablating elements occupies more space in a housing, where space is limited in a transducer assembly, especially when the transducer is at the tip of the catheter as used in an interventional approach. Additionally, a multi-element device is more expensive and inconvenient to manufacture, along with the complicated arrangements necessary for cooling the transducer elements. Further, multi-element devices are prone to misalignment, which may make them more difficult to use. Also, multi-element devices typically require more complex and expensive systems for their control and use.

Thus, additional improvements are still desired in the field of ultrasound devices with combined imaging and ablating capabilities. In particular, it would be desirable to provide a device with a single-crystal transducer assembly where all faces of the transducer crystal are cooled to protect and preserve the operating efficiency. It would also be desirable to provide such a system that is easy to use, easy to manufacture and that is lower in cost than current commercial systems.

2. Description of Background Art

Patents related to the treatment of atrial fibrillation include, but are not limited to the following: U.S. Pat. Nos. 7,393,325; 7,142,905; 6,997,925; 6,996,908; 6,966,908; 6,964,660; 6,955,173; 6,954,977; 6,953,460; 6,949,097; 6,929,639; 6,872,205; 6,814,733; 6,780,183; 6,666,858; 6,652,515; 6,635,054; 6,605,084; 6,547,788; 6,514,249; 6,502,576; 6,500,121; 6,416,511; 6,383,151; 6,305,378; 6,254,599; 6,245,064; 6,164,283; 6,161,543; 6,117,101; 6,064,902; 6,052,576; 6,024,740; 6,012,457; 5,629,906; 5,405,346; 5,314,466; 5,295,484; 5,246,438; 4,757,820 and 4,641,649.

Patent Publications related to the treatment of atrial fibrillation include, but are not limited to International PCT Publication Nos. WO 2005/117734; WO 1999/002096; and U.S. Patent Publication Nos. 2005/0267453; 2003/0050631; 2003/0050630; and 2002/0087151.

Scientific publications related to the treatment of atrial fibrillation include, but are not limited to: Haissaguerre, M. et al., *Spontaneous Initiation of Atrial Fibrillation by Ectopic Beats Originating in the Pulmonary Veins*, New England J Med., Vol. 339:659-666; J. L. Cox et al., *The Development of the Maze Procedure for the Treatment of Atrial Fibrillation*, Seminars in Thoracic & Cardiovascular Surgery, 2000; 12: 2-14; J. L. Cox et al., *Electrophysiologic Basis, Surgical Development, and Clinical Results of the Maze Procedure for Atrial Flutter and Atrial Fibrillation*, Advances in Cardiac Surgery, 1995; 6: 1-67; J. L. Cox et al., *Modification of the Maze Procedure for Atrial Flutter and Atrial Fibrillation. II, Surgical Technique of the Maze III Procedure*, Journal of Thoracic & Cardiovascular Surgery, 1995; 110: 485-95; J. L. Cox, N. Ad, T. Palazzo, et al. *Current Status of the Maze Procedure for the Treatment of Atrial Fibrillation*, Seminars in Thoracic & Cardiovascular Surgery, 2000; 12: 15-19; M. Levinson, *Endocardial Microwave Ablation: A New Surgical Approach for Atrial Fibrillation*; The Heart Surgery Forum, 2006; Maessen et al., *Beating Heart Surgical Treatment of Atrial Fibrillation with Microwave Ablation*, Ann Thorac Surg 74: 1160-8, 2002; A. M. Gillinov, E. H. Blackstone and P. M. McCarthy, *Atrial Fibrillation: Current Surgical Options and their Assessment*, Annals of Thoracic Surgery 2002; 74:2210-7; Sueda T., Nagata H., Orihashi K., et al., *Efficacy of a Simple Left Atrial Procedure for Chronic Atrial Fibrillation in Mitral Valve Operations*, Ann Thorac Surg 1997; 63:1070-1075; Sueda T., Nagata H., Shikata H., et al.; *Simple Left Atrial Procedure for Chronic Atrial Fibrillation Associated with Mitral Valve Disease*, Ann Thorac Surg 1996; 62:1796-1800; Nathan H., Eliakim M., *The Junction Between the Left Atrium and the Pulmonary Veins, An Anatomic Study of Human Hearts*, Circulation 1966; 34:412-422; Cox J. L., Schuessler R. B., Boineau J. P., *The Development of the Maze Procedure for the Treatment of Atrial Fibrillation*, Semin Thorac Cardiovasc Surg 2000; 12:2-14; and Gentry et al., *Integrated Catheter for 3-D Intracardiac Echocardiography and Ultrasound Ablation*, IEEE Transactions on Ultrasonics, Ferroelectrics, and Frequency Control, Vol. 51, No. 7, pp 799-807.

SUMMARY OF THE INVENTION

The present invention discloses a transducer assembly with combined imaging and therapeutic capabilities that may be used to create lesions in tissue. In preferred embodiments, the transducer assembly is used to ablate tissue to create a conduction block in the target tissue which blocks aberrant electrical pathways. Thus, the transducer assembly may be used as a treatment for fibrillation or other arrhythmias, as well as other conditions requiring creation of a lesion in tissue.

In a first aspect of the present invention, a transducer system comprises a transducer element comprising a proximal surface and a distal surface, and a first heat sink attached to the distal surface of the transducer element. The system also has a second heat sink attached to the proximal surface of the transducer element, and a base coupled to the first and second heat sinks The base is configured to allow fluid flow past the transducer element for cooling of the and distal surfaces of the transducer element, and the heat sinks The system may further comprise a tubular jacket configured to house the base, the transducer element, and the first and second heat sinks The tubular jacket may comprise at least one fluid exit port configured to allow fluid to exit the tubular jacket. The first heat sink may comprise a first bonding portion and a first substantially bent portion. The first bonding portion may be bonded to the distal surface of the transducer, and the first substantially bent portion may protrude proximally from the transducer element, thereby conducting heat away from the distal surface of the transducer element. The first bonding portion may comprise a material whose composition and dimension provides an acoustically matching layer on the distal surface of the transducer element. The first bonding portion may comprise a material chosen from the group consisting of aluminum, graphite, metal-filled graphite, ceramic, an amalgam of graphite and copper or tungsten, and an epoxy-filled metal. The bonding portion may be in electrical and/or thermal communication with the distal surface of the transducer element. Electrical communication between the bonding portion and the distal surface may be established by direct contact between the bonding portion and the distal surface. The direct contact may be controlled by surface roughness of the bonding portion and the distal surface.

The second heat sink may comprise a second bonding portion and a second substantially bent portion. The second bonding portion may be bonded to the proximal surface of the transducer, and the second substantially bent portion may protrude proximally from the transducer element, thereby conducting heat away from the proximal surface of the transducer element. The second bonding portion may comprise a material whose composition is acoustically mismatched to an acoustic impedance of the transducer element, thereby providing a reflective backing layer on the proximal surface of the transducer element. The second bonding portion may comprise a metal such as copper. An air pocket may be disposed between the proximal surface of the transducer and the second heat sink.

The transducer element may comprise a substantially flat circular disc, and the transducer element may operate at a first power level in a first frequency range and a second power level in a second frequency range. The first frequency range may be used for ultrasonically imaging tissue and the second frequency range may be used for creating tissue lesions. The first frequency range may be 5 MHz to 30 MHz and the second frequency range may be 10 to 18 MHz.

The first and second bonding portions may comprise a matrix containing perforations such that the first bonding portion is acoustically matched and the second bonding portion is acoustically mismatched to the acoustic impedance of the transducer element. The system may further comprise an elongate flexible shaft having a proximal end and a distal end, and the transducer may be disposed adjacent the distal end of the shaft. The system may also comprise a cooling fluid in fluid communication with the transducer. The system may comprise a temperature sensor adjacent the transducer for monitoring temperature of the transducer or cooling fluid flowing therepast. Adjustments to the cooling fluid flow rate or the transducer power levels may be made based on the monitored temperature.

In another aspect of the present invention, a method of ablating tissue comprises introducing an ablation device into a patient. The device comprises an ultrasound transducer element configured to operate at a first power level and at a second power level. The first power level is used for ultrasonically imaging tissue and identifying a target tissue, and the second power level is used for ablating the target tissue. Operating the transducer element at the first power level allows imaging of a portion of the tissue and identification of the target tissue. Operating at the second power level ablates the target tissue. The ultrasound transducer surfaces are cooled during operation.

The transducer element may comprise a proximal surface and a distal surface, and the device may further comprise first and second heat sinks bonded to the distal and proximal surfaces of the transducer element, respectively. The cooling step may comprise introducing fluid to the transducer element and to the first and second heat sinks during operation of the transducer element, thereby further cooling the transducer element. The transducer element may comprise first and second portions. The first portion may be configured to operate at the first power level and the second portion may be configured to operate at the second power level. The first portion may be operated at the first power level concurrently with operation of the second portion at the second power level. The introducing step may comprise passing the ablation device transseptally across a septal wall of the patient's heart. The introducing step may also comprise positioning the ablation device into a left atrium of the patient's heart. There may not be direct contact between the transducer and the target tissue.

These and other embodiments are described in further detail in the following description related to the appended drawing figures.

BRIEF DESCRIPTION OF THE DRAWINGS

FIGS. 2A-2D illustrate alternative embodiments of the transducer element.

DETAILED DESCRIPTION OF THE INVENTION

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

Figure 1A:
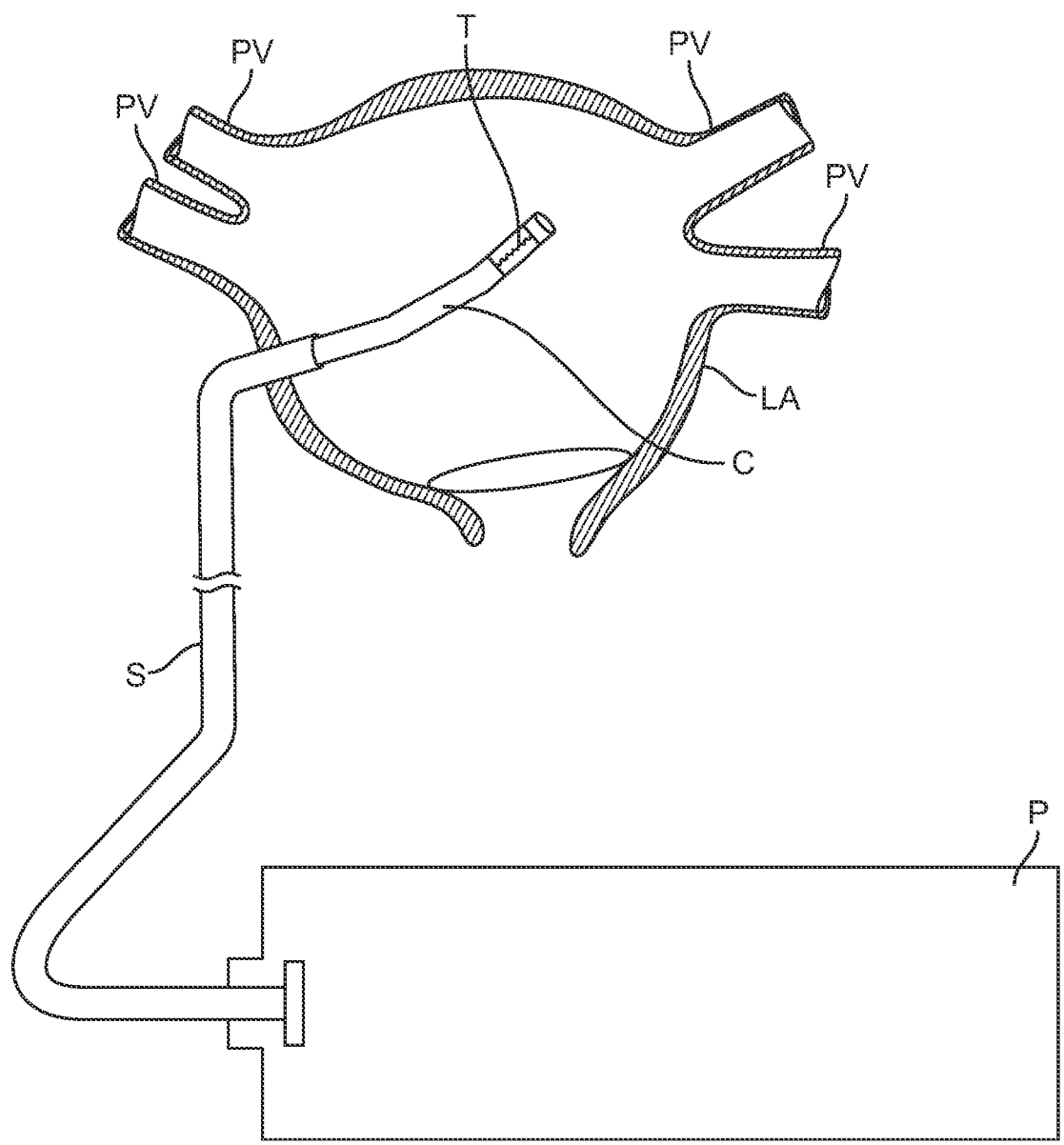
FIG. 1A illustrates an exemplary system for treating tissue using a transducer assembly.

The present invention relates to creating ablation zones in human tissue, and more specifically to transducer assemblies (or subassemblies) that are used for creating tissue lesions. FIG. 1A is a diagrammatic illustration of an exemplary embodiment of a system for creating ablation zones in human tissue, as described in the above referenced related parent applications. A catheter device C is housed within a sheath S. A proximal portion of the catheter C is coupled to a console P. A distal portion of the catheter C, comprising an ultrasonic transducer subassembly T, is introduced into the heart, preferably transseptally, into the left atrium (LA), adjacent the pulmonary veins PV of a patient. The transducer subassembly T is energized to provide ultrasonic energy for ablating tissue. The console P controls energy delivery to the transducer subassembly T, as well as movements of the distal portion of the catheter C to trace ablation paths. Additional details on the ablation system are disclosed in U.S. Provisional Patent Application No. 61/254,997 previously incorporated herein by reference.

For brevity, the transducer subassemblies are described herein with respect to one embodiment of a catheter for sensing and ablating tissue. However, the transducer assemblies of this invention may be utilized with any suitable device in both medical and non-medical fields.

The transducer subassemblies comprise transducer elements and are configured such that the same transducer element may be used to both image (for example, in A-mode) and ablate. The transducer elements may be in the shape of a disc, or other shapes may be used for the transducer elements. The transducer subassemblies are also configured for effective cooling of the transducer elements, in order to increase the efficiency of transduction. This is accomplished by affixing (e.g. by bonding, welding, snap fitting, etc.) a distal and a proximal heat sink to the transducer element, thereby conducting heat away from the transducer element. In order to further increase efficiency, the distal heat sink comprises an acoustically matching layer and the proximal heat sink comprises an acoustically mismatched backing layer. Additionally, each of the heat sinks is configured to allow for a cooling substance (e.g., a fluid such as saline, water) to be directed to and dissipate the heat from the proximal and distal surfaces (hereinafter also referred to as "faces") of the transducer element.

Figure 1B:
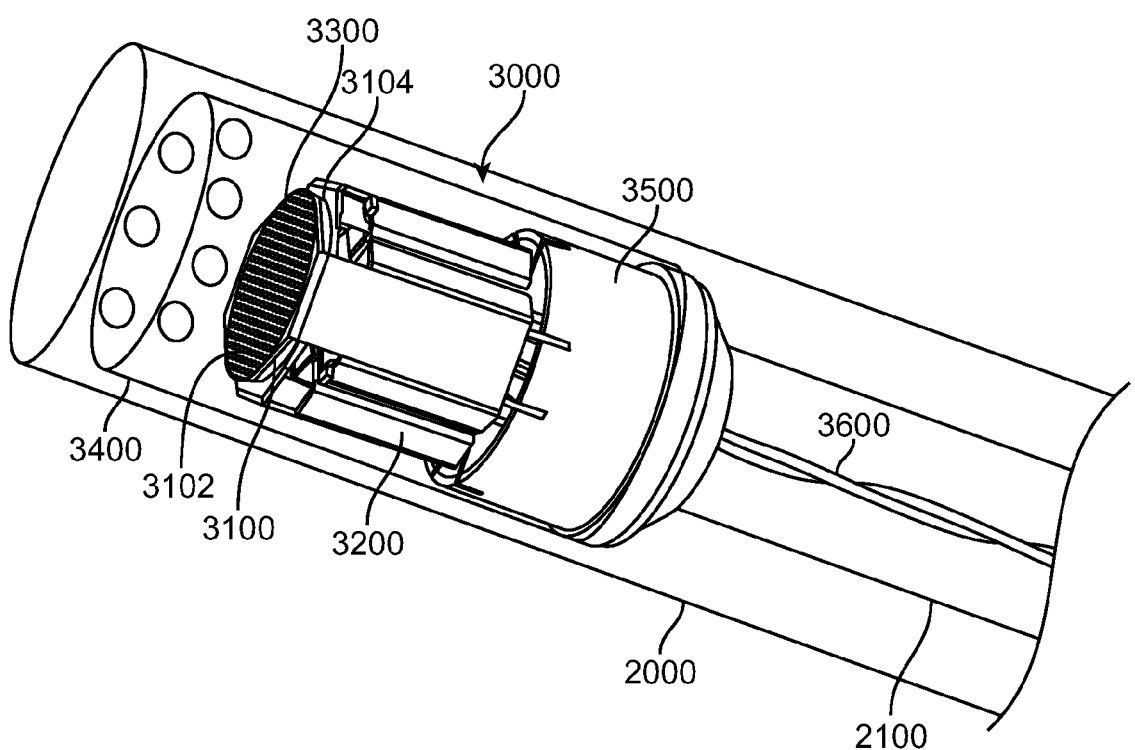
FIGS. 1B-1C illustrate exemplary embodiments of a transducer assembly.

As shown in FIG. 1B, a transducer subassembly 3000 is placed at or near the distal portion of a catheter 2000 and contained within a tubular jacket 3400. The catheter 2000 may be any suitable catheter and comprises at least one lumen 2100. The components of transducer subassembly 3000 are shown in an assembled view in FIG. 1B, and in an exploded view in FIG. 1C. The transducer subassembly 3000 comprises a transducer element 3100 having a distal face 3102 and a proximal face 3104. The transducer subassembly 3000 further comprises heat sinks that serve to cool the transducer element 3000 by conducting heat away from it. Specifically, the transducer subassembly 3000 comprises a distal heat sink 3300 bonded to the distal face 3102 of the transducer element 3100, and a proximal heat sink 3200 bonded to the proximal face 3104 of the transducer element 3100.

The heat sinks are further configured to increase the operating efficiency of the transducer element 3000 through acoustic matching and acoustic reflection. Specifically, and as described in further detail below, the distal heat sink 3300 comprises an acoustically matching layer portion, i.e., a portion whose composition and thickness provides a ¼ wavelength matching layer between the transducer element 3100 and any fluid in front of the transducer subassembly 3000. The proximal heat sink 3200 comprises an acoustically mismatched layer portion, i.e., a portion whose composition is acoustically mismatched to the acoustic impedance of the transducer element 3100, thereby reflecting ultrasound waves emanating from the transducer element 3100 back towards the transducer element 3100. These portions are more fully described below.

Figure 1C:
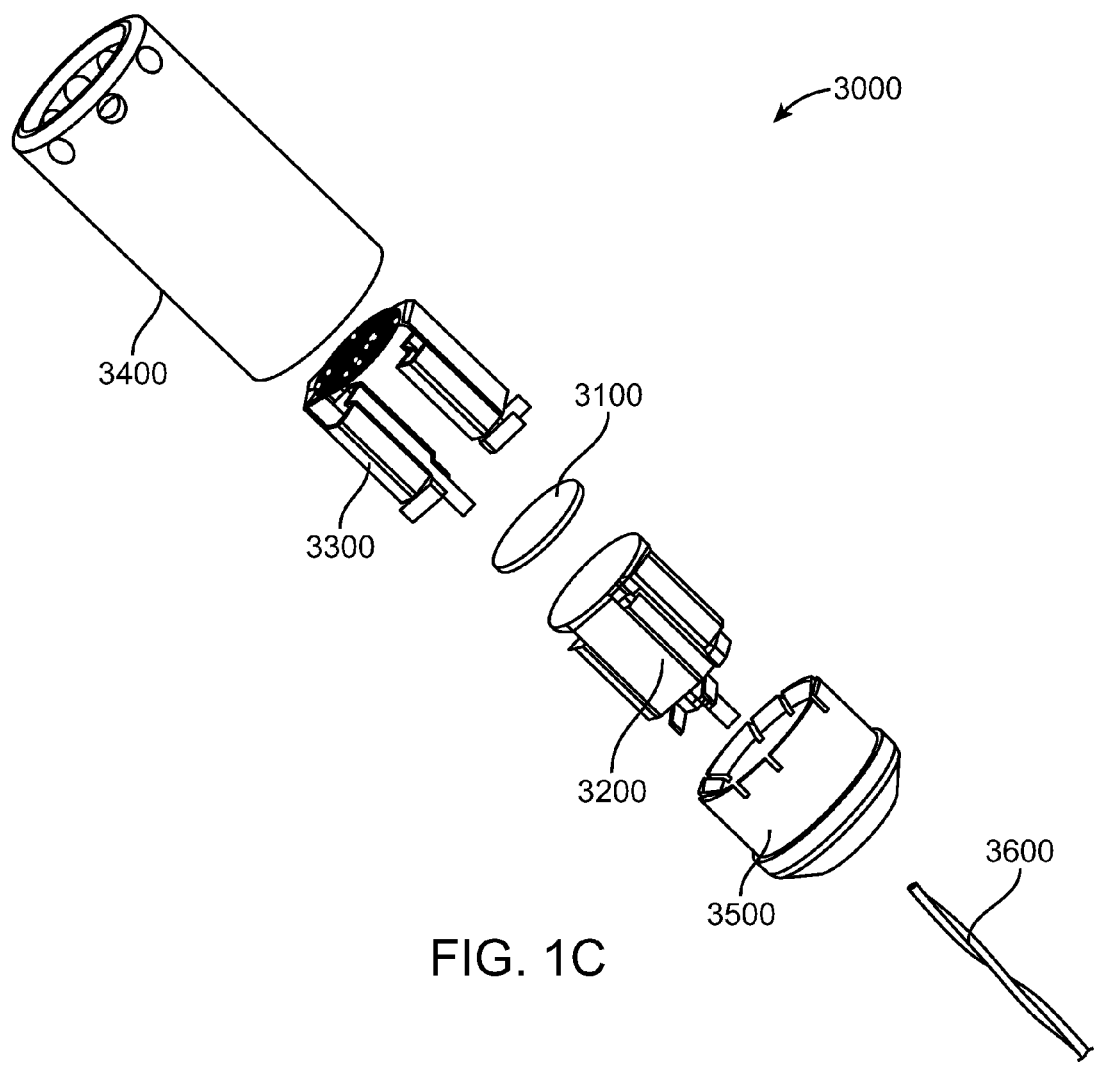

The transducer subassembly 3000 also comprises a base 3500 anchoring the heat sinks 3200 and 3300, with the transducer element 3100 bonded between the heat sinks The transducer subassembly 3000 is powered using one or more electrical cables 3600 bonded to each of the heat sinks 3200 and 3300. These electrical cables 3600 are exemplarily provided through a pair of twisted wires, as shown in FIGS. 1B and 1C. As will be appreciated, they could also be coaxial or separate untwisted wires. The heat sinks 3200 and 3300 comprise electrical attachments (not shown) for electrically coupling the heat sinks 3200 and 3300 to the electrical cables 3600, thereby providing electrical power to the transducer element 3100. The transducer element 3100 comprises electrode platings on the distal and proximal faces in order to distribute the electrical energy over the faces of the transducer element 3100.

As disclosed herein, the transducer element 3100 comprises a single transducer element. However, those skilled in the art would appreciate that this single element may be comprised of smaller sub-elements. The transducer is of a suitable size to fit into a catheter configured to be introduced percutaneously into the atria of the heart. For example, in one embodiment, the transducer diameter is less than 0.2 inches, and preferably less than 0.15 inches.

Further, the transducer element may comprise a variety of geometries, as well as a variety of acoustically active and inactive portions. Such transducer element properties in turn influence the transducer's imaging and ablative properties, such as the shape of the created ablation lesions. These concepts of using transducer elements of various shapes and sizes (sub-elements) are further described below.

For example, in the embodiment shown in FIGS. 1B and 1C, the transducer element 3100 is a flat, circular disc that transmits ultrasound energy from its proximal and distal faces. The transducer element 3100 may alternatively have more complex geometry, such as either concave or convex, to achieve an effect of a lens or to assist in apodization (i.e., in selectively decreasing the vibration of a portion or portions of the surfaces of the transducer element 3100) and management of the propagation of the ultrasound beam.

Other exemplary transducers are shown in FIGS. 2A through 2D. For example, as shown in FIGS. 2A and 2B, the transducers 3100a and 3100b include at least one acoustically inactive portion 4200, with the remainder of the transducer surface comprising an acoustically active portion. In these embodiments, the acoustically inactive portion 4200 does not emit an energy beam when the transducer is energized, or may alternatively emit an energy beam with a very low (substantially zero) energy. The acoustically inactive portion 4200 has several functions. For instance, the shape of a lesion produced by ablating tissue using such a transducer may correspond with the shape of the acoustically active ablating portions. For example, in the circular embodiment shown in FIGS. 1B and 1C, the shape of the lesion will be tear-drop shaped. However, in the annular embodiment shown in FIG. 2A, the shape of the lesion will be approximately tooth-shaped or a blunted tear-shaped. This is because the acoustically inactive portion 4200 in FIG. 2A will preclude prolonged ablation at the corresponding central portion of the tissue. Since prolonged ablation of tissue creates a deeper ablation, the presence of acoustically inactive portion 4200 precludes ablation from reaching further into the tissue at the central portion. The lesion thus is approximately tooth-shaped or blunted tear-shaped, as illustrated by the exemplary lesion shape L of FIG. 2A, rather than tear-shaped.

In addition to influencing the shape of the created ablation lesion, acoustically inactive portion 4200, in any of the embodiments shown, further functions to aid in the temperature regulation of the transducer elements 3100a and 3100b, i.e., in preventing the transducer elements from becoming too hot.

Acoustically inactive portions may be created in a variety of ways. In one embodiment, an acoustically inactive portion 4200 is a hole or gap defined by the boundary of the acoustically active region of the transducer element. In such an embodiment, an optional coolant source may be coupled to (or in the case of a coolant fluid, it may flow through) the hole or gap defined by the transducer element to further cool and regulate the temperature of the transducer element.

In another embodiment, the acoustically inactive portion 4200 may comprise a material composition with different properties from that of the active region of the transducer element. For example, the acoustically inactive material may be made of a metal, such as copper, which further functions to draw or conduct heat away from the transducer element. Alternatively, the acoustically inactive portion 4200 may be made from the same material as the transducer element, but with the electrode plating removed or disconnected from the electrical attachments. The acoustically inactive portion 4200 may be disposed along the full thickness of the transducer element, or may alternatively be a layer of material on or within the transducer element that has a thickness less than the full thickness of the transducer element.

For example, as shown in FIG. 2A, the transducer element 3100a is a doughnut-shaped transducer that comprises a hole (or acoustically inactive portion) 4200 in the center portion of the otherwise circular disc-shaped transducer element. The transducer element 3100a of this embodiment has a circular geometry, but may alternatively be elliptical, polygonal as shown in FIG. 2B, or any other suitable shape. The transducer element 3100a includes a singular, circular acoustically inactive portion 4200, but may alternatively include any suitable number of acoustically inactive portions 4200 of any suitable geometry, as shown in FIG. 2B. Exemplary geometries of acoustically inactive portions include circular, square, rectangular, elliptical, polygon, or any other shaped region. The total energy emitted from the transducer element is related to the acoustically active surface area of the transducer element. Therefore, the size and location of acoustically inactive portion(s) 4200 may sufficiently reduce the heat build-up in the transducer element, while allowing the transducer element to provide as much output energy as possible or as desired.

As disclosed herein, the transducer elements may optionally be configured to operate at more than one frequency. This allows them to be used for multi-frequency ablating or for contemporaneous ablation and diagnosis. For example, such a multi-frequency transducer element may be operated intermittently at a first power level using a first frequency range that is used to image a portion of the tissue in order to identify a target tissue, and operated at a second power level using a second frequency range that is used to ablate the target tissue. In one embodiment, the imaging frequency is in the range of about 5 MHz to 30 MHz, and the ablation frequency is preferably in the range of 5 to 25 MHz, more preferably in the range 8 to 20 MHz, and even more preferably in the range 10 to 18 MHz. The transducers achieving these configurations are shown to exemplarily be annular transducers or grid arrays.

As shown in FIGS. 2C and 2D, the transducer elements 3100c and 3100d are configured to be capable of transmitting at more than one frequency. Specifically, as shown in FIG. 2C, the transducer element 3100c includes a plurality of annular transducer portions 4400. The plurality of annular transducer portions is a plurality of concentric rings, but may alternatively have any suitable configuration with any suitable geometry, such as elliptical or polygonal. Optionally, the transducer element 3100c includes one or more acoustically inactive portions 4200, such as the center portion of the transducer 3100c. The plurality of annular transducer portions 4400 includes at least a first annular portion and a second annular portion. The first annular portion may have material properties that differ from those of the second annular portion, such that the first annular portion emits a first energy beam that is different from a second energy beam emitted by the second annular portion. Furthermore, the first annular portion may be energized with a different frequency, voltage, duty cycle, power, and/or for a different length of time from the second annular portion. Alternatively the first annular portion may be operated in a different mode from the second annular portion. For example, the first annular portion may be operated in a therapy mode, such as ablation mode, which delivers a pulse of ultrasound energy sufficient for heating the tissue. The second annular portion may be operated in an imaging mode, such as A-mode, which delivers a pulse of ultrasound of short duration, which is generally not sufficient for heating of the tissue but functions to detect characteristics of the target tissue and/or environment in and around the ultrasound delivery system. The first annular portion may further include a separate electrical attachment from that of the second annular portion.

In a another embodiment of a multi-frequency transducer element shown in FIG. 2D, the transducer element 3100d includes a grid of transducer portions 4600. The grid of transducer portions 4600 has any suitable geometry such as circular, rectangular, elliptical, polygonal, or any other suitable geometry. The transducer element 3100d in this variation may further include one or more transducer portions that are acoustically inactive. The grid of transducer portions 4600 includes at least a first transducer portion and a second transducer portion. The first transducer portion and the second transducer portion are portions of a single transducer with a single set of material properties. The first transducer portion is energized with a different frequency, voltage, duty cycle, power, and/or for a different length of time from the second transducer portion. Furthermore, the first transducer portion may be operated in a different mode from the second transducer portion. For example, similar to the description above, the first transducer portion may operate in a therapy mode, such as ablate mode, while the second transducer portion may operate in a imaging mode, such as A-mode. The first transducer portion may further include a separate electrical attachment from that of the second transducer portion. For example, the first transducer portion may be located towards the center of the transducer element 3100d and the second transducer portion may be located towards the outer portion of the transducer element 3100d. Further, the second transducer portion may be energized while the first transducer portion remains inactive. In other embodiments, the first transducer portion has material properties that differ from those of the second transducer portion, such that the first transducer portion emits a first energy beam that is different from a second energy beam emitted from the second transducer portion. In such an embodiment, the first transducer portion may also be energized with a different frequency, voltage, duty cycle, power, and/or for a different length of time from the second transducer portion.

Figure 3:
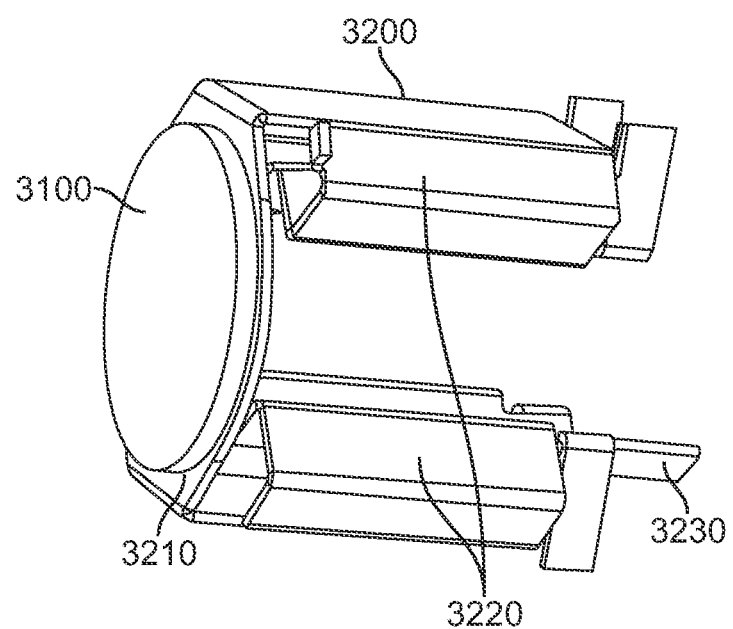
FIG. 3 illustrates the transducer element with a first heat sink.

Turning now to the heat sinks 3200 and 3300, FIG. 3 shows the proximal heat sink 3200. In this embodiment, the proximal heat sink 3200 comprises a bonding portion 3210 and a substantially bent portion forming legs 3220 that are generally orthogonal to the bonding portion 3210. The proximal heat sink further comprises at least one electrical attachment 3230. Similarly, the distal heat sink comprises an electrical attachment 3330 (shown in FIG. 4). The electrical wires 3600 are connected to the electrical attachments 3230 and 3330. Unlike conventional electrical attachments to a transducer crystal, where the electrical leads are connected to the opposing faces of the crystal, the disclosed arrangement eliminates "hot spots" and results in a uniform electrical power density across the surface of the crystal. Additionally, this results in an easier assembly or manufacturing process.

The bonding portion 3210 is bonded to the proximal face of the transducer element 3100 with a suitable bonding material such as an epoxy to form a bond layer. Though shown as substantially flat in this embodiment, one skilled in the art will appreciate that the bonding portion 3210 may be any suitable configuration such as a concave portion to still maintain the functionality described herein. The substantially bent portion 3220 comprises legs, or elements that protrude proximally from the transducer element 3100. Further, the bent portion 3220 is configured in a manner to allow for fluid to flow through the bent portion and also allows the fluid to surround and cool the proximal face of the transducer element 3100. The fluid that could be accommodated within the bent portion could be any suitable fluid that achieves an appropriate balance between having an effective heat sink and minimizing acoustic reverberations that degrade image performance. The proximal heat sink 3200 is formed from a suitable material such as copper of a suitable thickness. The thickness of the material for this heat sink preferably ranges between 0.0001 inches to 0.01 inches for a copper heat sink.

Proximal heat sink 3200 serves to cool the proximal face of the transducer by conducting and dissipating the heat away from the transducer element 3100. Heat from the transducer element 3100 is absorbed by the bonding portion 3210, and conducted to the bent portion 3220 where it is dissipated into the circulating fluid. This dissipation provides some cooling to the proximal face of the transducer element 3100. Additionally, the bent portion 3220 is configured in a manner to allow for fluid to surround and cool the proximal face of the transducer element 3100. For example, as shown in FIG. 3, the bent portion 3220 provides for one or more pockets behind the transducer element 3100 where a fluid may be introduced to flow and cool both the transducer element 3100 as well as the proximal heat sink 3200 that has dissipated heat from the proximal face of the transducer element 3100.

As described above, in addition to dissipating the heat, the proximal heat sink 3200 also serves as a heat spreader to reduce hot spots in the transducer element 3100, and thereby preserve it over its entire face. Without this heat spreading, the center of the transducer element 3100 would be substantially hotter than the rest of the transducer element 3100.

The bonding portion 3210 can be configured to maximize the amount of reflected energy transmitted from the transducer element 3100. Since many metals suitable for heat sink applications have acoustic impedances that are not too dissimilar from PZT, the boundary between PZT and the heat sink itself does not provide a very effective reflective interface. However, another material immediately proximal to the heat shield could be selected so that it provides an efficient acoustic reflector. For example, air provides an excellent acoustic mismatch, as does water, and therefore acts as good reflectors. Water is preferred since it also acts as a thermal conductor, even though it is not quite as effective a reflector as air. Air could be used, provided that it does not interfere with the flow of cooling fluid around the transducer assembly. To accomplish this, the bonding portion of 3210 could be constructed from two metal layers capturing a third thin layer of air in between. Alternatively, a backing material may be located proximal to the proximal heat sink 3200 to provide an acoustically absorptive medium to minimize reverberations to further optimize imaging performance. Such backing materials may optionally be made of combinations of epoxy, metal particles, tungsten and the like.

Additionally or alternatively, the transducer element 3100 or the transducer subassembly 3000 may be placed on a tripod-style structure (not shown) such that the proximal surface of the transducer element 3100 faces into the tripod. In this configuration, a pocket forms in the space between the transducer element 3100 and the tripod base. This pocket serves as an alternative backing with the same two-fold purpose. First, it is acoustically mismatched and thereby reflective of the ultrasound waves emanating from the transducer element 3100. Second, as fluid (for example saline or water) is introduced into the transducer assembly 3000, the pocket also allows for the fluid to come into contact with the transducer element 3100 and thereby provide for additional cooling.

Alternatively, another suitable acoustically mismatched material with reasonable thermal conduction could be used in place of fluid. Such materials include metal with trapped air, for example steel wool or porous metal with entrapped air. For example, the rear of the PZT may comprise a thin heat spreader comprising the entire rear face with a pocket of porous metal attached behind. As another example, the center of the PZT could be further cooled by providing a thermally conducting center post as part of the heat sink, allowing an annular ring of air to be trapped behind the bonding portion 3210.

Figure 4:
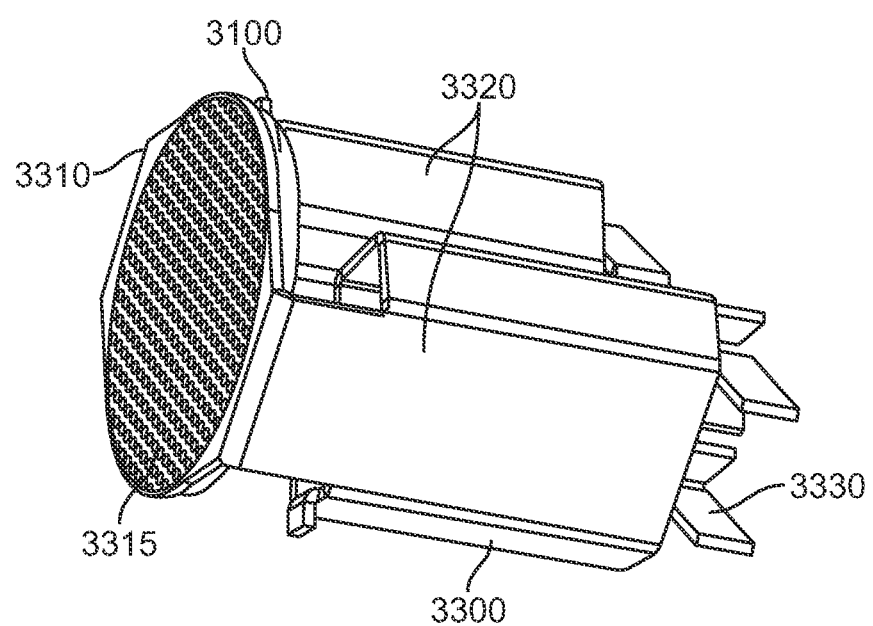
FIG. 4 illustrates the transducer element with a second heat sink.

As mentioned above, additional cooling can be provided by a distal heat sink 3300 (which also serves as a heat spreader) for distributing the heat and cooling the distal face of the transducer element 3100. As shown in FIG. 4, the distal heat sink 3300 also comprises a bonding portion 3310 and a substantially bent portion 3320 that is orthogonal to the flat portion 3310. The distal heat sink further comprises at least one electrical attachment 3330. The distal heat sink 3300 is configured such that the bonding portion 3310 is bonded to the distal face of the transducer element 3100. The substantially bent portion 3320 comprises elements or legs that protrude proximally from the transducer element 3100. Thus the bent portion 3320 of the distal heat sink 3300 is adjacent to the bent portion 3220 of the proximal heat sink 3200. As mentioned above, the bonding portion 3310 is further configured to serve as an acoustically matching layer for the transducer element 3100. To provide an acoustically matching composition that is also thermally conductive, the bonding portion 3310 is made of a suitable material such as aluminum; other such suitable materials include graphite, metal-filled graphite or ceramic, or an amalgam of graphite and copper or tungsten, in suitable thickness that range from 0.026 inches to 0.00026 inches so that it is ¼ wavelength at the desired frequency. The bonding portion 3310 is bonded to the distal face of the transducer element 3100 with a suitable bonding material such as an epoxy to form a bond layer.

Additionally and optionally, the bonding portion 3310 comprises perforations or holes 3315 that may be filled with epoxy applied in a layer of a suitable thinness to enhance the acoustic impedance matching. Perforations in the distal matching layer can be accomplished in many ways. The perforated structure is made of a combination of metal matrix containing open spaces, later to be filled with an epoxy material. For example, the metal matrix can be a wire grid. Alternatively, the perforated structure may be a matrix of epoxy film, and the holes may be filled with a metal such as aluminum. Additionally, the ratio of epoxy to the metal mixture is configured to enhance acoustic impedance matching. The acoustic impedance is determined by the acoustic impedance of the two composite materials, and the ratio of the mixture. For example, using aluminum and EPO-TEK® 377 (Epoxy Technology, Inc., Billerica, Mass.) the appropriate ratio is 35-60% volume fraction of epoxy and a good acoustic impedance matching is achieved at a 40-50% volume fraction of epoxy and an ideal match about 41%. Additionally, the perforations or holes 3315 have a sufficiently small diameter as compared to the wavelength of the ultrasonic beam, thereby allowing the bonding portion 3310 to appear homogeneous to the propagating waves emanating from the transducer element 3100.

Similar to the construction of using bonding portion 3310 with perforations or holes to achieve acoustic impedance matching, the bonding portion 3210 at proximal surface of the transducer crystal also may benefit from using perforations or holes in the material used to achieve acoustic impedance mismatch. Such materials may include copper, tungsten and the like. Alternatively, an epoxy layer with metal particles sprinkled in it and a distribution of holes or perforations may achieve the same purpose of providing acoustic impedance mismatch.

Both non-conductive and conductive epoxy (with metal particles such as silver) could be used to form either the proximal or distal bond layer. In one embodiment, the epoxy is exemplarily a non-conductive epoxy of a low viscosity (e.g., EPO-TEK® 377). The epoxy is applied in a layer of suitable thinness to minimize its impact on acoustic impedance matching, while maximizing thermal conduction to cool the transducer 3100. Additionally, the bond layers are also configured to electrically connect the heat sinks 3310 and 3210 to the transducer 3100. This is successfully accomplished without the use of conductive epoxy by configuring the transducer 3100 faces and the bonding portions 3310 and 3210 to be rough. Thereafter, the distal and the proximal faces of the transducer element 3100 are bonded to their relevant heat sinks with electrically non-conductive epoxy. Each bond layer is of sufficient thinness to allow the surface roughness of the transducer 3100 to electrically contact the surface roughness of the heat sinks 3310 and 3210. This allows the rough surfaces of the transducer element 3100 to come into direct electrical contact with their relevant heat sinks, thereby obviating the need for using electrically conductive epoxy (which may degrade with heat). Thus, electrical conduction occurs via the contact points between the rough surfaces of the transducer element 3100 and the heat sinks, rather than through the epoxy.

Figure 5:
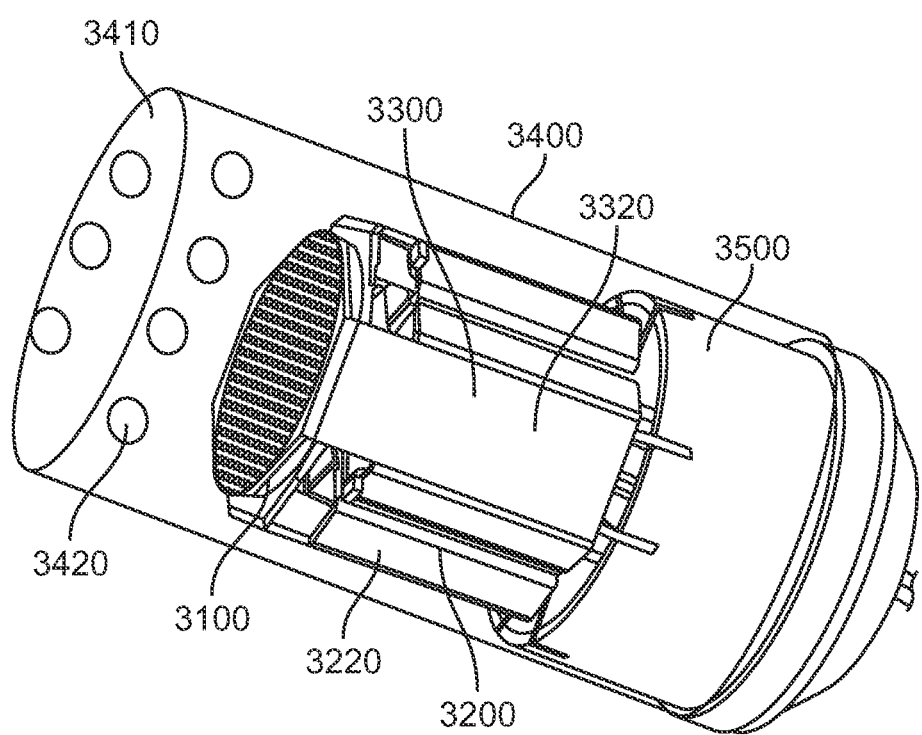
FIG. 5 illustrates the transducer assembly in a tubular jacket.

Additionally and optionally, parylene or any such suitable coating is disposed on the bonding portion 3310 of the distal heat sink 3300 to act as an additional matching layer. One result of the coating may be to thus produce a second acoustic matching layer for increased efficiency of transducer element 3100 conduction and to further optimize the wide bandwidth performance. The thickness of this parylene coat is ¼ of the target ultrasound wavelength. Optionally, both heat sinks 3200 and 3300 are coated with parylene or any such suitable coatings to provide electrical isolation. Further, heat sinks are anodized to provide electrical isolation while maximizing thermal conduction. The transducer subassembly 3000 is located within a tubular jacket 3400, as shown in FIG. 5. The tubular jacket 3400 is a hollow cylinder with a proximal and distal end. The transducer subassembly 3000 is placed into the tubular jacket 3400 such that the distal end of the tubular jacket protrudes a suitable distance, for example between 1 mm to 5 mm beyond the distal end of the transducer subassembly 3000. The distal end of the tubular jacket 3400 comprises a distal opening 3410, and fluid exit ports 3420 located near the distal opening. Cooling of the transducer element 3100 may be accomplished by introducing a cooling fluid or gel, such as saline, water, or any physiologically compatible fluid or gel, into the proximal end of the tubular jacket 3400. The cooling fluid has a lower temperature relative to the temperature of the transducer element 3100. The cooling fluid flows along the bent portions 3220 and 3320 of heat sinks 3200 and 3300 and over both bonding portions 3210 and 3310 and exits through the distal opening 3410, the fluid exit ports 3420, or any combination thereof. Optionally, the exit ports 3420 may be in the form of a grating, a screen, holes, drip holes, a weeping structure, or any of a number of suitable apertures.

Additionally, any or all of the metal components described in transducer subassembly 3000 are provided with a plating of a suitable biocompatible material such as gold. Such plating is provided to the individual components before the transducer assembly is assembled.

In an exemplary embodiment, the temperature of the cooling fluid or gel is sufficiently low that it cools the transducer element 3100 and, optionally, the target tissue. In this embodiment, the temperature of the fluid or gel is between approximately −5 and body temperature. In a second embodiment, the temperature of the cooling fluid or gel is within a temperature range such that it cools the transducer element 3100, but does not cool the target tissue, and may actually warm the target tissue. The fluid or gel may alternatively be any suitable temperature, including room temperature, to sufficiently cool the transducer element 3100.

The invention described above has the advantage of keeping the smaller transducer assembly cool. As previously mentioned, the transducer diameter is small enough (less than 0.2 inches, and ideally less than 0.15 inches) to fit into the tip of a catheter and yet generate power density levels that are high enough to create tissue lesions (about 50 watts/cm$^2$ to 2500 watts/cm$^2$). This invention keeps the transducer assembly cool in order to create tissue lesions efficiently.

Figure 6:
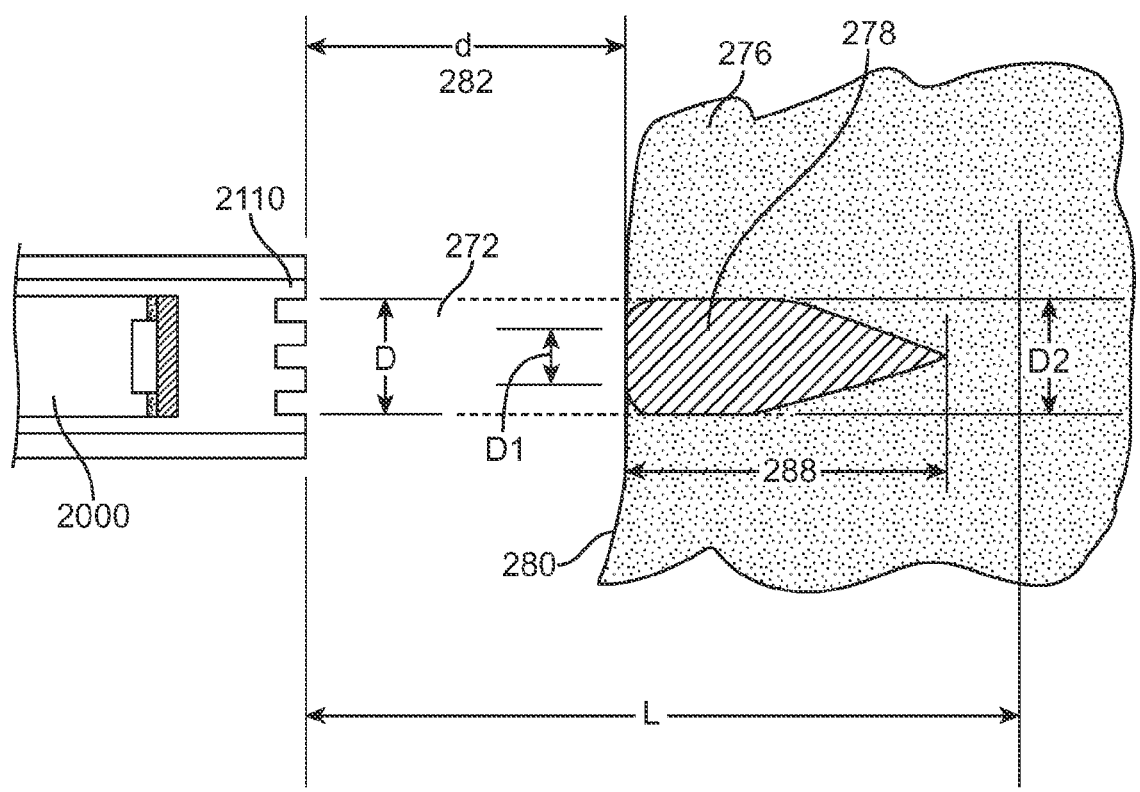
FIG. 6 illustrates an ablation pattern in tissue.

We now turn to describing the formation of lesions. The interaction of the ultrasound beam with the tissue is shown in FIG. 6. The tissue 276 is presented to the ultrasound beam 272 within a collimated length L. The front surface 280 of the tissue 276 is at a distance d (282) away from the distal tip 2110 of the catheter 2000. As the ultrasound beam 272 travels through the tissue 276, its energy is absorbed and scattered by the tissue 276, and most of the ultrasound energy is converted to thermal energy. This thermal energy heats the tissue to temperatures higher than the surrounding tissue. The result is a heated zone 278 which has a typical shape of an elongated tear drop. The diameter D1 of the zone 278 is smaller than the transducer aperture diameter D at the tissue surface 280, and further, the outer layer(s) of tissue 276 remain substantially undamaged. This is due to the thermal cooling provided by the surrounding fluid which is flowing past the tissue surface 280. More or less of the outer layers of tissue 276 may be spared or may remain substantially undamaged, depending on the amount that the tissue surface 280 is cooled and/or depending on the characteristics of the ultrasound delivery system (including the transducer element 3100 the ultrasound beam 272, the ultrasound energy and the frequency). The energy deposited in the ablation zone 278 interacts with the tissue such that the endocardial surface remains pristine and/or not charred. As the ultrasound beam 272 travels deeper into the tissue 276, thermal cooling is provided by the surrounding tissue, which is not as efficient as that on the surface. The result is that the ablation zone 278 has a larger diameter D2 than D1, as determined by the heat transfer characteristics of the surrounding tissue as well as the continued input of the ultrasound energy from the beam 272. During this ultrasound-tissue interaction, the ultrasound energy is being absorbed by the tissue 276, and less of it is available to travel further into the tissue. Thus a correspondingly smaller diameter heated zone is developed in the tissue 276, and the overall result is the formation of the heated ablation zone 278 which is in the shape of an elongated tear drop limited to a depth 288 into the tissue 276.

Figure 7A:
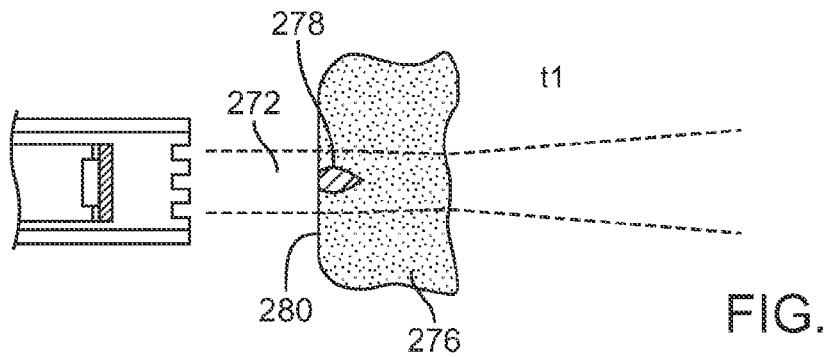
FIGS. 7A-7D illustrate the progression of ablation in tissue.
Figure 7B:
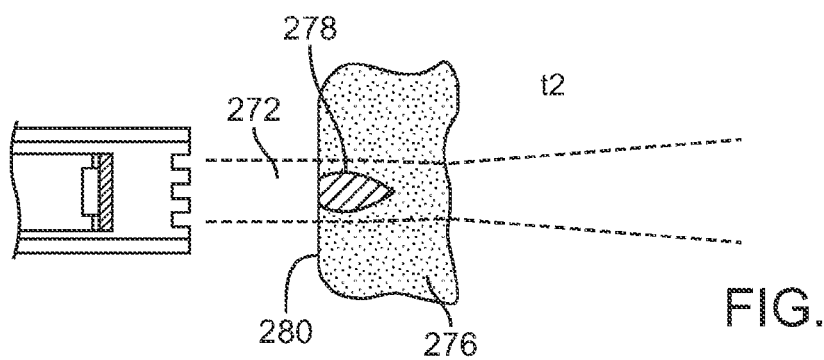
Figure 7C:
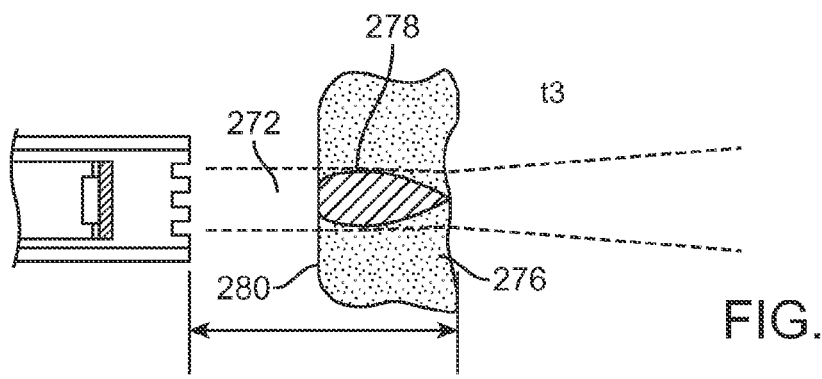
Figure 7D:
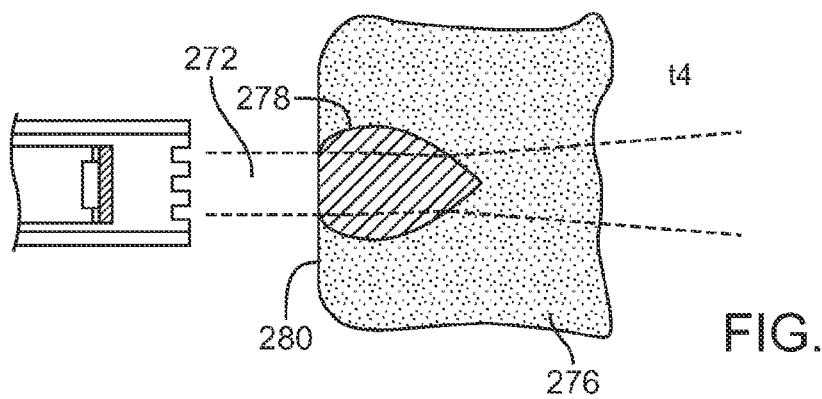

The formation of the ablation zone (including the size of the ablation zone and other characteristics) is dependent on time, as shown in FIGS. 7A-7D, which show the formation of the lesion at times t1, t2, t3 and t4, respectively. As the sound beam 272 initially impinges on the front surface 280 of the tissue 276 at time t1, heat is created which begins to form the lesion 278 (FIG. 7A). As time passes on to t2 and t3 (FIGS. 7B and 7C), the ablation zone 278 continues to grow in diameter and depth. This time sequence from t1 to t3 takes as little as about 1 to 5 seconds, or preferably about 3 to 5 seconds, depending on the ultrasound energy density. As the incidence of the ultrasound beam 272 is continued beyond time t3, the ablation lesion 278 grows slightly in diameter and length, and then stops growing due to the steady state achieved in the energy transfer from its ultrasound form to the thermal form balanced by the dissipation of the thermal energy into the surrounding tissue. The example shown in of FIG. 7D shows the lesion after an exposure t4 of approximately 30 seconds to the ultrasound beam 272. Thus the lesion reaches a natural limit in size and does not grow indefinitely.

The shape of the lesion or ablation zone 278 formed by the ultrasound beam 272 depends on factors such as the ultrasound beam 272, the transducer element 3100 (including the material, the geometry, the portions of the transducer element 3100 that are energized and/or not energized, etc.), any matching layers and/or backings present, the electrical signal from the source of electrical energy (including the frequency, the voltage, the duty cycle, the length and shape of the signal, etc.), and the duration of energy delivery. The characteristics of the target tissue include the thermal transfer properties and the ultrasound absorption, attenuation, and backscatter properties of the target tissue and surrounding tissue. The size and characteristics of the ablation zone 278 also depend on the frequency and voltage applied to the transducer element 3100 to create the desired ultrasound beam.

Figure 8:
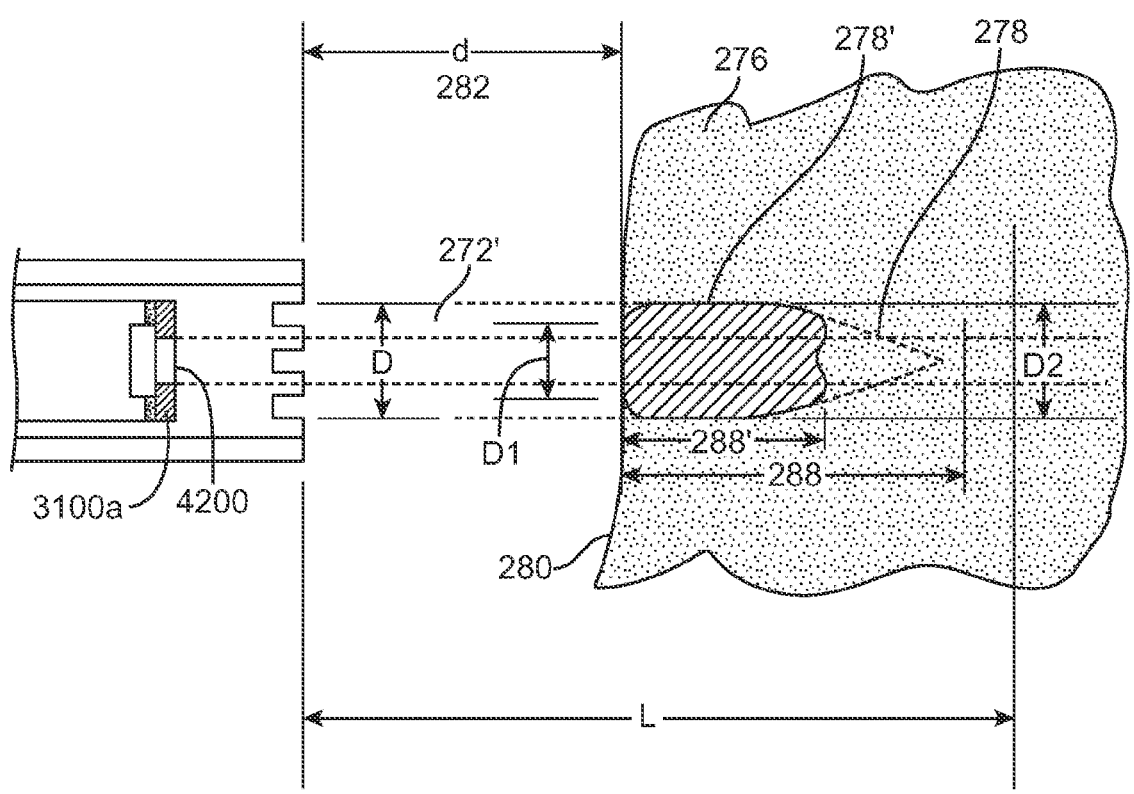
FIG. 8 illustrates an alternative lesion shape.

As mentioned above, properties such as the shape and construction of a transducer element influence the ablation lesions created by the transducer element. The particular example lesion shown in FIGS. 7A through 7D is a tear-shaped lesion, for example as produced by a transducer element 3100 comprising a circular disc. A second variation of ablation shape is shown in FIG. 8, where the ablation zone 278' has a shorter depth 288'. In this variation, the lesion 278' has a more blunt shape than the ablation zone 278 of FIG. 6. One possible lesion geometry of this second variation may be a tooth-shaped geometry, as shown in FIG. 8, though the geometry may alternatively have a blunted tear shape, a circular shape, or an elliptical shape. As shown in FIG. 8, zone 278' (similarly to zone 278 in FIG. 6) has a diameter D1 smaller than the diameter D of the beam 272' at the tissue surface 280 due to the thermal cooling provided by the surrounding fluid flowing past the tissue surface 280. This variation in lesion geometry is produced by a transducer 3100a having an acoustically inactive portion 4200 located at its center, i.e., a doughnut-shaped transducer which emits an ultrasound beam 272' that is generally more diffused, with a broader, flatter profile, than the ultrasound beam 272 shown in FIG. 6. The ultrasound beam 272' emitted from such a doughnut-shaped transducer, as shown in FIG. 8, has reduced peak intensity along the midline of the energy beam (as shown in cross section by the dotted lines in FIG. 8). With this ultrasound-tissue interaction, the reduced peak intensity along the midline of the energy beam is absorbed by the tissue, and less and less of the energy is available to travel further into the tissue, thereby resulting in a blunter lesion as compared to the first variation.

The ultrasound energy density determines the speed at which the ablation occurs. The acoustic power delivered by the transducer element 3100, divided by the cross sectional area of the beamwidth, determines the energy density per unit time. In the present embodiments, effective acoustic power ranges preferably from 0.5 to 25 watts, more preferably from 2 to 10 watts, and even more preferably from 2 to 7 watts. The corresponding power densities range from approximately 50 watts/cm$^2$ to 2500 watts/cm$^2$). These power densities are developed in the ablation zone. As the beam diverges beyond the ablation zone, the energy density falls such that ablation will not occur, regardless of exposure time.

The transducer subassembly 3000 may additionally be coupled to a sensor (not shown). One variation of a sensor is a temperature sensor. The temperature sensor functions to detect the temperature of the surrounding environment, the transducer element 3100, and/or the temperature of any other suitable element or area. The sensor may also be used to monitor temperature of cooling fluid as it flows past the transducer. The temperature sensor is a thermocouple, but may alternatively be any suitable temperature sensor, such as a thermistor or an infrared temperature sensor. Optionally, the temperature sensor is coupled to the transducer, for example, on the proximal face. Temperature information gathered by the sensor is used to manage the delivery of continuous ablation energy to the tissue 276 during therapy, as well as to manage the temperature of the target tissue and/or the ultrasound delivery system. In one embodiment, the sensor has a geometry that is substantially identical to the geometry of the transducer element 3100, so that the area diagnosed by the sensor is substantially identical to the area to be treated by the transducer element 3100. Alternatively, the sensor has a smaller geometry to minimize interfering with the delivery of ultrasound energy, but may be located in a region that is a local hot spot. For example, a small thermocouple mounted in the center of the proximal heat spreader 3200 monitors the temperature at the hottest spot of the transducer assembly. Additional details on temperature sensors are disclosed in applications previously incorporated by reference above.

Alternatively, in a second variation of a sensor, the same ultrasound transducer element 3100 serves as a sensor and is used for the purpose of tissue detection. On the one hand, in order to achieve ablation, the transducer element 3100 is used to generate and deliver an ultrasound beam of sufficient energy to the tissue in a manner such that the energy input exceeds the thermal relaxation provided by the cooling due to the surrounding tissue. This mode of energizing the ultrasound transducer element 3100 is termed as the ablation mode. On the other hand, the transducer element 3100 may be used to image tissue or to detect tissue characteristics, by utilizing an ultrasound signal optimized for tissue sensing which is generally not sufficient for heating of the tissue. One such ultrasound imaging technique is referred to in the art as A-Mode, or Amplitude Mode imaging. This mode of energizing the transducer element 3100 is termed as the imaging mode. The imaging mode is utilized in directing the therapy provided by the ablation of the tissue. The transducer element 3100 can be used in the imaging mode in order to detect the gap (namely, the distance of the tissue surface from the distal tip of the catheter 2000), the thickness of the tissue targeted for ablation, characteristics of the ablated tissue, the incident beam angle, or any other suitable parameter or characteristic of the tissue and/or the environment around the ultrasound delivery system, such as temperature, thickness and ablation depth. Additional details on these and other applicable features are described in the disclosures previously incorporated by reference.

Additionally and optionally, the ultrasound delivery system of the preferred embodiments includes a processor, coupled to the sensor, that controls the electrical attachments and/or the electrical signal delivered to the electrical attachments, based on the information obtained by the sensor. The processor may be a conventional processor, or it may alternatively be any suitable device to perform the desired processing functions.

The processor receives information from the sensor, such as information related to the distance between the catheter and the tissue (i.e., the gap distance), the thickness of the tissue targeted for ablation, the characteristics of the ablated tissue, or any other suitable parameter or characteristic. Based on this information, the processor controls the ultrasound beam emitted by the transducer element 3100 by modifying the electrical signal sent to the transducer element 3100 via the electrical attachment. This may include modifying the frequency, the voltage, the duty cycle, the length of the pulse, and/or any other suitable parameter. The processor may also control the ultrasound beam in multi-element transducers by controlling which portions of the transducer element are energized, and/or by controlling the frequency, voltage, duty cycle, etc. at which various portions of the transducer element may be energized. Additionally, the processor may further be coupled to a fluid flow controller. The processor may control the fluid flow controller in order to increase or decrease fluid flow based on the detected characteristics of the ablated tissue, of the unablated or target tissue, the temperature of the cooling fluid, tissue and/or energy source, and/or any other suitable conditions. Further, the processor may control the fluid flow controller in order to maintain the transducer element 3100 within a desired operating range of temperatures. Further, the motion of the transducer to create a lesion line or shape in the tissue may be controlled either by an operator or via one or more motors under processor control.

By controlling the ultrasound beam and/or the cooling of the targeted tissue or transducer element 3100, the shape of the ablation zone 278 can be controlled. For example, the depth 288 of the ablation zone can be controlled such that a transmural or substantially transmural lesion is achieved. Further, the nature of the lesion can be controlled by controlling the speed of the beam. The speed at which the beam moves along the tissue determines the amount of energy deposited in the tissue. Thus, for example, slower speeds result in longer dwell times, thereby increasing the energy transferred to the tissue and, hence, creating deeper lesions. Additionally, the processor functions to minimize the possibility of creating a lesion beyond the targeted tissue, for example, beyond the outer atrial wall. If the sensor detects that the lesion and/or the ablation window is about to extend beyond the outer wall of the atrium, or that the depth of the lesion has reached or exceeded a preset depth, the processor turns off the power generator and/or ceases to send electrical signals to the transducer and/or moves the beam.

Additionally, the processor may function to maintain a preferred gap distance between the transducer and the surface of the target tissue. The gap distance is preferably between 2 mm and 25 mm, more preferably between 2 mm and 20 mm, and even more preferably between 2 mm and 15 mm. If the sensor detects that the lesion and/or the ablation window is about to extend beyond the outer wall of the atrium or is not reaching the outer wall of the atrium, or that the depth of the lesion has not reached or has exceeded a preset depth, the processor may reposition the energy delivery system. For example, as the catheter 2000 is rotated, the ablation window sweeps an ablation path (such as a circular or elliptical ablation path) creating a section of a conical shell. However, if the sensor determines that the ablation window is not reaching the wall of the atrium, the processor may move the elongate member forwards or backwards along the Z-axis, or indicate that it should be moved, in order to adjust for possible variations in anatomy. In such an embodiment, the operator can reposition the catheter 2000, or the processor may be coupled to a motor drive unit or other control unit that functions to position the catheter 2000.

While the above transducer elements and transducer subassemblies have been described in the context of ablation catheters, it should be understood that the transducer elements and transducer subassemblies described herein can be used as part of any device configured to ultrasonically image and/or ablate tissue. Additionally, while the above is a complete description of the preferred embodiments of the invention, various alternatives, modifications, and equivalents may be used. Therefore, the above description should not be taken as limiting the scope of the invention which is defined by the appended claims.

What is claimed is:

1. A transducer system comprising:
   a transducer element comprising a proximal surface and a distal surface, wherein the proximal surface is a continuous surface;
   a processor coupled to the transducer element, wherein the processor controls a voltage to operate the transducer element at a first power level and a second power level, wherein the transducer element is configured for both imaging and ablation of the tissue, wherein the transducer element is operated at the first power level to image the tissue, wherein the transducer element is operated at the second power level to ablate the tissue, wherein the first power level is different than the second power level, and wherein the transducer element is alternating between imaging and ablation;
   a first bonding portion attached to the distal surface of the transducer element, wherein the first bonding portion serves as a first acoustic matching layer and as a distal heat sink;
   a coating on the first bonding portion that serves as a second acoustic matching layer;
   a proximal heat sink having a second bonding portion attached to the proximal surface of the transducer element, wherein the second bonding portion is bonded to the continuous proximal surface of the transducer element to conduct heat away from the transducer element; and
   a base coupled to the proximal heat sink, wherein the base is configured to anchor the proximal heat sink and allow fluid flow past the transducer element for cooling the proximal surface and the distal surface of the transducer element.

2. The system of claim 1, further comprising a tubular jacket configured to house the base, the transducer element, the proximal heat sink and the distal heat sink, wherein the tubular jacket comprises at least one fluid exit port configured to allow fluid to exit the tubular jacket.

3. The system of claim 1, wherein the first bonding portion is a material chosen from the group consisting of aluminum, graphite, metal-filled graphite, ceramic, copper, an amalgam of graphite and copper, an amalgam of graphite and tungsten, and an epoxy-filled metal.

4. The system of claim 1, wherein a thickness of the second bonding portion is 0.0001 to 0.01 inches.

5. The system of claim 1, wherein the second bonding portion comprises a material whose composition is acoustically mismatched to an acoustic impedance of the transducer element, thereby providing a reflective backing layer on the proximal surface of the transducer element.

6. The system of claim 1, further comprising an air pocket disposed between the proximal surface of the transducer and the proximal heat sink.

7. The system of claim 1, wherein the transducer element comprises a flat circular disc.

8. The system of claim 7, wherein the transducer element has a dimension less than 0.2 inches, thereby allowing the transducer element to fit in a catheter.

9. The system of claim 1, wherein the transducer element operates at the first power level in a first frequency range and the second power level in a second frequency range, the second frequency range being different from the first frequency range.

10. The system of claim 9, wherein the first frequency range is 5 MHz to 30 MHz and the second frequency range is 10 to 18 MHz.

11. The system of claim 1, wherein the second bonding portion comprises perforations such that the second bonding portion is acoustically mismatched to an acoustic impedance of the transducer element.

12. The system of claim 1, further comprising an elongate flexible shaft having a proximal end and a distal end, and wherein the transducer element is disposed adjacent the distal end of the shaft.

13. The system of claim 1, further comprising a cooling fluid in fluid communication with the transducer element.

14. The system of claim 1, further comprising a temperature sensor adjacent the transducer element for monitoring temperature.

15. The transducer system of claim 1, wherein the coating that serves as the second acoustic matching layer is parylene.

16. A method of imaging and ablating tissue, said method comprising:
 introducing an ablation device into a patient, wherein the device comprises:
 a) a transducer element comprising a proximal surface and a distal surface, wherein the proximal surface is a continuous surface;
 b) a first bonding portion attached to the distal surface of the transducer element, wherein the first bonding portion serves as a first acoustic matching layer and as a distal heat sink; wherein a coating on the first bonding portion serves as a second acoustic matching layer;
 c) a proximal heat sink having a second bonding portion attached to the proximal surface of the transducer element, wherein the heat sink comprises a bent portion, wherein the second bonding portion is bonded to the proximal surface of the transducer element, and wherein the bent portion forms one or more legs that protrude proximally from the transducer element and is configured to allow fluid flow therethrough in a direction along the legs; and
 d) a base coupled to the proximal heat sink, wherein the base is configured to anchor the proximal heat sink,
 operating the transducer element at a first power level to image a portion of the tissue and identify a target tissue, and at a second power level to ablate the target tissue, wherein the first power level is different than the second power level, and wherein the transducer element is alternating between imaging and ablation;
 conducting heat away from the transducer element to the bent portion using the second bonding portion of the proximal heat sink; and
 flowing fluid through the bent portion and past the transducer element, wherein fluid flow is in a direction along the legs;
 wherein the steps of conducting heat away and flowing fluid provide cooling of the proximal surface and the distal surface of the transducer element.

17. The method of claim 16, further comprising monitoring temperature of the fluid and adjusting fluid flow based on the monitored temperature.

18. The method of claim 16, wherein the transducer element comprises first and second portions, wherein the operating of the transducer element at the first power level is performed by the first portion, and the operating of the transducer element at the second power level is performed by the second portion.

19. The method of claim 18, wherein the operating of the transducer element at the first power level is performed concurrently with the operating of the transducer element at the second power level.

20. The method of claim 16, wherein the introducing step comprises passing the ablation device transseptally across a septal wall of the patient's heart.

21. The method of claim 16, wherein the introducing step comprises positioning the ablation device into a left atrium of the patient's heart.

22. The method of claim 16, wherein there is no contact between the transducer element and the target tissue.

23. The method of claim 16, further comprising monitoring temperature of the transducer element and adjusting either the first or the second power level based on the monitored temperature.

24. A transducer system comprising:
 a transducer element comprising a proximal surface and a distal surface;
 a first bonding portion attached to the distal surface of the transducer element wherein the first bonding portion serves as a first acoustic matching layer and as a distal heat sink;
 a coating on the first bonding portion that serves as a second acoustic matching layer;
 a proximal heat sink having a second bonding portion attached to the proximal surface of the transducer element; and
 a base coupled to the proximal heat sink, wherein the base is configured to anchor the proximal heat sink; and
 wherein the proximal heat sink comprises a bent portion, and wherein the bent portion comprises a plurality of legs that protrude proximally from the transducer element and form a plurality of elongate channels configured to allow fluid flow therethrough in a direction along the legs to cool the transducer element.

* * * * *